US011603518B2

(12) United States Patent
Onishi et al.

(10) Patent No.: US 11,603,518 B2
(45) Date of Patent: Mar. 14, 2023

(54) DORSALLY-DERIVED OLIGODENDROCYTE PROGENITOR CELLS FROM HUMAN PLURIPOTENT STEM CELLS

(71) Applicant: Asterias Biotherapeutics, Inc., Carlsbad, CA (US)

(72) Inventors: Kento Onishi, Oakland, CA (US); Nathan C. Manley, San Jose, CA (US); Craig R. Halberstadt, Pleasanton, CA (US); Erik M. Whiteley, Concord, CA (US)

(73) Assignee: ASTERIAS BIOTHERAPEUTICS, INC., Carlsbad, CA (US)

( * ) Notice: Subject to any disclaimer, the term of this patent is extended or adjusted under 35 U.S.C. 154(b) by 225 days.

(21) Appl. No.: 16/750,975

(22) Filed: Jan. 23, 2020

(65) Prior Publication Data

US 2020/0231932 A1    Jul. 23, 2020

Related U.S. Application Data

(60) Provisional application No. 62/796,077, filed on Jan. 23, 2019.

(51) Int. Cl.
*C12N 5/0793* (2010.01)

(52) U.S. Cl.
CPC ........ *C12N 5/0619* (2013.01); *C12N 2501/11* (2013.01); *C12N 2501/115* (2013.01); *C12N 2506/03* (2013.01)

(58) Field of Classification Search
CPC .............. C12N 5/0619; C12N 2506/03; C12N 2506/02
USPC ................................. 435/377, 325
See application file for complete search history.

(56) References Cited

U.S. PATENT DOCUMENTS

| | | |
|---|---|---|
| 6,280,718 B1 | 8/2001 | Kaufman et al. |
| 6,642,048 B2 | 11/2003 | Xu et al. |
| 6,800,480 B1 | 10/2004 | Bodnar et al. |
| 7,285,415 B2 | 10/2007 | Keirstead et al. |
| 7,390,659 B2 | 6/2008 | Jessell et al. |
| 7,524,489 B2 | 4/2009 | Messina et al. |
| 7,579,188 B2 | 8/2009 | Keirstead et al. |
| 8,137,969 B2 | 3/2012 | Reubinoff et al. |
| 8,227,247 B2 | 7/2012 | Zhang et al. |
| 9,238,794 B2 | 1/2016 | Shogbon et al. |
| 9,862,925 B2 | 1/2018 | Aharonowiz et al. |
| 10,138,292 B2 | 11/2018 | Tryggvason et al. |
| 10,286,009 B2 | 5/2019 | Wirth, III et al. |
| 10,301,592 B2 | 5/2019 | Fossati et al. |
| 10,450,546 B2 | 10/2019 | Goldman et al. |
| 10,676,716 B2 | 6/2020 | Fossati et al. |
| 2004/0009593 A1 | 1/2004 | Keirstead et al. |
| 2005/0031598 A1 | 2/2005 | Levenberg et al. |
| 2010/0015702 A1 | 1/2010 | Rao et al. |
| 2010/0158878 A1 | 6/2010 | Capela et al. |
| 2010/0159595 A1 | 6/2010 | Zhang et al. |
| 2010/0166720 A1 | 7/2010 | Vanderhaeghen et al. |
| 2010/0239541 A1 | 9/2010 | Johe et al. |
| 2011/0059055 A1 | 3/2011 | Goldman et al. |
| 2012/0100113 A1 | 4/2012 | Tesar et al. |
| 2012/0177614 A1 | 7/2012 | Kido |
| 2013/0004467 A1 | 1/2013 | Goldman et al. |
| 2013/0143805 A1 | 6/2013 | Whittaker et al. |
| 2013/0210109 A1 | 8/2013 | Lebkowski et al. |
| 2013/0280219 A1 | 10/2013 | Shiels |
| 2014/0170634 A1 | 6/2014 | Woods |
| 2015/0017139 A1 | 1/2015 | Huang et al. |
| 2015/0050667 A1 | 2/2015 | Carson et al. |
| 2016/0015707 A1 | 1/2016 | Tesar et al. |
| 2016/0030490 A1 | 2/2016 | Lanza et al. |
| 2016/0152950 A1 | 6/2016 | Zhang et al. |
| 2017/0224740 A1 | 8/2017 | Sing et al. |
| 2020/0087622 A1 | 3/2020 | Nair et al. |
| 2020/0231932 A1 | 7/2020 | Onishi et al. |

FOREIGN PATENT DOCUMENTS

| | | |
|---|---|---|
| CN | 102160546 A | 8/2011 |
| CN | 102803472 A | 11/2012 |
| KR | 20090035372 A | 4/2009 |

(Continued)

OTHER PUBLICATIONS

Zhang (2018, Stem Cell Research and Therapy, 9:67, 13 pages).*
International Search Report and Written Opinion issued in International Application No. PCT/US20/014834, dated Apr. 23, 2020, 11 Pages.
Ahmed et al. (Apr. 2014) "Decorin Blocks Scarring and Cystic Cavitation in Acute and Induces Scar Dissolution in Chronic Spinal Cord Wounds", Neurobiology of Disease, 64:163-176.
Amit et al. (Jan. 22, 2003) "Human Feeder Layers for Human Embryonic Stem Cells", Biology of Reproduction, 68(6):2150-2156.
Armstrong et al. (Nov. 1990) "Type 1 Astrocytes and Oligodendrocyte-type 2 Astrocyte Glial Progenitors Migrate Toward Distinct Molecules", Journal of Neuroscience Research, 27(3):400-407.

(Continued)

*Primary Examiner* — Valarie E Bertoglio
(74) *Attorney, Agent, or Firm* — Mintz, Levin, Cohn, Ferris, Glovsky and Popeo, P.C.

(57) ABSTRACT

Methods for differentiating human pluripotent stem cells to dorsal neuroectoderm progenitors and further to glial progenitor cells and oligodendrocyte progenitor cells (OPCs) using inhibitors of BMP signaling and MAPK/ERK signaling are provided. Also provided are cells and cellular compositions obtained by such methods, and uses of such cells. Further provided are methods and protocols for efficiently differentiating human pluripotent stem cells to OPCs in the absence of the ventralizing morphogen SHH or a SHH signaling activator. The methods of the present disclosure reproducibly produce dorsal neuroectoderm progenitor cells by day 7 of the differentiation process, glial progenitor cells by day 21 of the differentiation process and OPCs by day 42 of the differentiation process.

27 Claims, 7 Drawing Sheets

(56) References Cited

FOREIGN PATENT DOCUMENTS

| WO | 0128342 A1 | 4/2001 |
|---|---|---|
| WO | 0151616 A2 | 7/2001 |
| WO | 03020920 A1 | 3/2003 |
| WO | 2004007665 A2 | 1/2004 |
| WO | 2010151782 A1 | 12/2010 |
| WO | 2014124087 A1 | 8/2014 |
| WO | 2015143342 A1 | 9/2015 |
| WO | 2015179822 A1 | 11/2015 |
| WO | 2016103269 A1 | 6/2016 |
| WO | 2017132596 A1 | 8/2017 |
| WO | 2017173064 A1 | 10/2017 |

OTHER PUBLICATIONS

Avantaggiato et al. (Jul. 1995) "Developmental Analysis of Murine Promyelocyte Leukemia Zinc Finger (PLZF) Gene Expression: Implications for the Neuromeric Model of the Forebrain Organization", Journal of Neuroscience, 15(7):4927-4942.

Bansod et al. (2017) "Hes5 Regulates the Transition Timing of Neurogenesis and Gliogenesis in Mammalian Neocortical Development", Development, 3156-3167.

Briscoe et al. (Jun. 2001) "A Hedgehog-insensitive Form of Patched Provides Evidence for Direct Long-range Morphogen Activity of Sonic Hedgehog in the Neural Tube", Mol. Cell., 7(6):1279-1291.

Cai et al. (Jan. 6, 2005) "Generation of Oligodendrocyte Precursor Cells from Mouse Dorsal Spinal Cord Independent of Nkx6 Regulation and Shh Signaling", Neuron, P41-53.

Chambers et al. (Mar. 1, 2009) "Highly Efficient Neural Conversion of Human ES And iPS Cells By Dual Inhibition Of SMAD Signaling", Nature Biotechnology, 27(3):275-280.

Chiang et al. (Oct. 3, 1996) "Cyclopia and Defective Axial Patterning in Mice Lacking Sonic Hedgehog Gene Function", Nature, 383(6599):407-413.

Dai et al. (Jul. 2003) "The Trophic Role of Oligodendrocytes in the Basal Forebrain", The Journal of Neuroscience, 23 (13):5846-5853.

Debnath et al. (Jul. 2003) "Morphogenesis and Oncogenesis of MCF-10A Mammary Epithelial Acini Grown in Three-Dimensional Basement Membrane Cultures", Methods, 30(3):256-268.

Douvaras et al. (Jul. 2, 2015) "Generation and Isolation of Oligodendrocyte Progenitor Cells From Human Pluripotent Stem Cells", Nature Protocols, 1143-1154.

Dreau et al. (Dec. 2012) "Dorsal-ventral Patterning of the Neural Tube: a Tale of Three Signals", Developmental Neurobiology, 72(12):1471-1481.

Du et al. (Jun. 15, 2002) "Oligodendrocytes as Providers of Growth Factors", Journal of Neuroscience Research, 68 (6):647-654.

Ericson et al. (Nov. 15, 1996) "Two critical periods of Sonic Hedgehog signaling required for the specification of motor neuron identity", Cell, 87(4):661-673.

Fitzgerald et al. (Oct. 27, 2006) "Characterization of Neogenin-expressing Neural Progenitor Populations and Migrating Neuroblasts in the Embryonic Mouse Forebrain", Neuroscience, 142(3):703-716.

Gallo et al. (Apr. 15, 1996) "Oligodendrocyte Progenitor Cell Proliferation and Lineage Progression Are Regulated by Glutamate Receptor-Mediated K+ Channel Block", Journal of Neuroscience, 16(8):2659-2670.

Genbacev et al. (May 2005) "Serum-Free Derivation of Human Embryonic Stem Cell Lines on Human Placental Fibroblast Feeders", Fertility and Sterility, 83(5):1517-1529.

Huang et al. (Oct. 2018) "Functions of EpCAM in Physiological Processes and Diseases (Review)", International Journal of Molecular Medicine, 42(4):1771-1785.

Keirstead et al. (May 11, 2005) "Human Embryonic Stem Cell-Derived Oligodendrocyte Progenitor Cell Transplants Remyelinate and Restore Locomotion After Spinal Cord Injury", Journal of Neuroscience, 25(19):4694-4705.

Kim et al. (2012) "Highly Pure and Expandable PSA-NCAM-Positive Neural Precursors from Human ESC and iPSC-Derived Neural Rosettes", PLoS One, 7(7):e39715:12 pages.

Kim et al. (Mar. 23, 2019) "Pluripotent Stem Cell-derived Cerebral Organoids Reveal Human Oligodendrogenesis With Dorsal and Ventral Origins", BIORXIV, 31 Pages.

Krebsbach et al. (Aug. 1, 2017) "The Role of Integrin α6 (CD49f) in Stem Cells: More than a Conserved Biomarker", Stem Cells and Development, 26(15):1090-1099.

Kutejova et al. (Mar. 21, 2016) "Neural Progenitors Adopt Specific Identities by Directly Repressing All Alternative Progenitor Transcriptional Programs", Developmental Cell, 36(6):639-653.

Lee et al. (Jan. 2005) "Establishment and Maintenance of Human Embryonic Stem Cell Lines on Human Feeder Cells Derived From Uterine Endometrium Under Serum-Free Condition", Biology of reproduction, 72(1):42-49.

Lee et al. (1999) "The Specification of Dorsal Cell Fates in the Vertebrate Central Nervous System", Annual Review of Neuroscience, 22:261-294.

Lin et al. (Aug. 2017) "Bioinformatic Analysis Reveals Potential Properties of Human Claudin-6 Regulation and Functions", Oncology Report, 38(2):875-885.

Lippmann et al. (Apr. 14, 2015) "Deterministic HOX Patterning in Human Pluripotent Stem Cell-Derived Neuroectoderm", Stem Cell Reports, 14(4):632-644.

Manley et al. (Oct. 2017) "Human Embryonic Stem Cell-Derived Oligodendrocyte Progenitor Cells: Preclinical Efficacy and Safety in Cervical Spinal Cord Injury", Stem Cells Translational Medicine, 6(10): 1917-1929.

Marklund et al. (Jan. 1, 2014) "Detailed Expression Analysis of Regulatory Genes in the Early Developing Human Neural Tube", Stem Cells Dev., 23(1):5-15.

Milner et al. (Jan. 1997) "Contrasting Effects of Mitogenic Growth Factors on Oligodendrocyte Precursor Cell Migration", Glia, 19(1):85-90.

Orentas et al. (Jun. 1999) "Sonic Hedgehog Signaling is Required During the Appearance of Spinal Cord Oligodendrocyte Precursors", Development, 126(11):2419-2429.

Patterson et al. (Jan. 2012) "Defining the Nature of Human Pluripotent Stem Cell Progeny", Cell Research, 22(1):178-193.

Petit et al. (Sep. 2011) "Adult Spinal Cord Radial Glia Display a Unique Progenitor Phenotype", PLoS ONE, 6(9):e24538:15 pages.

Piao et al. (Feb. 5, 2015) "Human Embryonic Stem Cell-derived Oligodendrocyte Progenitors Remyelinate the Brain and Rescue Behavioral Deficits Following Radiation", Cell Stem Cell, 16(2):198-210.

Priest et al. (Sep. 8, 2015) "Preclinical safety of human embryonic stem cell-derived oligodendrocyte progenitors supporting clinical trials in spinal cord injury", Regenerative Medicine, 10(8):939-958.

Rathjen et al. (1998) "Properties and Uses of Embryonic Stem Cells: Prospects for Application to Human Biology and Gene Therapy", Reproduction, Fertility and Development, 10(1):31-47.

Ravanelli et al. (Dec. 1, 2015) "Motor Neurons and Oligodendrocytes Arise From Distinct Cell Lineages by Progenitor Recruitment", Genes Dev., 29(23):2504-2515.

Richards et al. (Sep. 2002) "Human Feeders Support Prolonged Undifferentiated Growth of Human Inner Cell Masses and Embryonic Stem Cells", Nature Biotechnology, 20(9):933-936.

Robertson E.J. (1987) "Teratocarcinomas and Embryonic Stem Cells: A Practical Approach.", IRL Press Ltd., 2 Pages.

Rodrigues et al. (Jun. 6, 2017) "Defined and Scalable Differentiation of Human Oligodendrocyte Precursors From Pluripotent Stem Cells in a 3d Culture System", Stem Cell Reports, 8(6):1770-1783.

Rodriguez et al. (Nov. 2018) "The Endocannabinoid 2-arachidonoylglycerol Regulates Oligodendrocyte Progenitor Cell Migration", Biochem Pharmacol., 157:180-188.

Rosenzweig et al. (Oct. 14, 2015) "The Axon-glia Unit in White Matter Stroke: Mechanisms of Damage and Recovery", Brain Res, 1623:123-134.

Rosler et al. (Feb. 2004) "Long-Term Culture of Human Embryonic Stem Cells in Feeder-Free Conditions", Developmental Dynamics, 229(2):259-274.

(56) References Cited

OTHER PUBLICATIONS

Rowitch HD. (May 2004) "Glial Specification in the Vertebrate Neural Tube", Nature Reviews Neuroscience, 5 (5):409-419.
Stacpoole et al. (Oct. 31, 2013) "High Yields of Oligodendrocyte Lineage Cells From Human Embryonic Stem Cells at Physiological Oxygen Tensions for Evaluation of Translational Biology", Stem Cell Reports, 1(5):437-450.
Thomson et al. (Nov. 6, 1998) "Embryonic Stem Cell Lines Derived from Human Blastocysts", Science, 282 (5391):1145-1147.
Vallstedt et al. (Jan. 6, 2005) "Multiple Dorsoventral Origins of Oligodendrocyte Generation in the Spinal Cord and Hindbrain", Neuron, 55-67.
Wang et al. (Feb. 7, 2013) "Human Ipsc-derived Oligodendrocyte Progenitor Cells Can Myelinate and Rescue a Mouse Model of Congenital Hypomyelination", Cell Stem Cell, , 12(2):252-264.
Wiles MV. (1993) "Embryonic Stem Cell Differentiation In Vitro", Methods in Enzymology, 225:900-918.
Wilkins et al. (Aug. 14, 2001) "A Role for Oligodendrocyte-Derived IGF-1 in Trophic Support of Cortical Neurons", Glia, 36(1):48-57.
Woo et al. (Aug. 17, 2009) "Notch Signaling Is Required for Maintaining Stem-Cell Features of Neuroprogenitor Cells Derived From Human Embryonic Stem Cells", BMC Neuroscience, 10(97): 12 pages.
Wu et al. (Aug. 25, 2013) "Combined Transplantation of Gdas(Bmp) and Hr-decorin in Spinal Cord Contusion Repair", Neural Regeneration Research, 8(24):2236-2248.
Xu et al. (Mar. 2005) "Basic Fibroblast Growth Factor Supports Undifferentiated Human Embryonic Stem Cell Growth Without Conditioned Medium", Stem Cells, 23(3):315-323.
Xu et al. (Oct. 2001) "Feeder-free Growth of Undifferentiated Human Embryonic Stem Cells", Nature Biotechnology, 19(10):971-974.
Yamashita et al. (Feb. 13, 2017) "Differentiation of Oligodendrocyte Progenitor Cells From Dissociated Monolayer and Feederfree Cultured Pluripotent Stem Cells", PLOS One, pp. 16.
Zhang et al. (Sep. 3, 2014) "An RNA-Sequencing Transcriptome and Splicing Database of Glia, Neurons, and Vascular Cells of the Cerebral Cortex", The Journal of Neuroscience, 34(36):11929-11947.
Zhu et al. (Nov. 2011) "Dorsally-derived Oligodendrocytes in the Spinal Cord Contribute to Axonal Myelination During Development and Remyelination Following Focal Demyelination", Glia, 59(11):1612-1621.
(2018) Enhanced Proliferation of Primary Nscs and Sustained Differentiation Into Precursors Using Heat-stable bFGF, Gibco, 3 pages.
European Search Report issued in European Application Application No. 17851575.5, dated Mar. 24, 2020, 6 pages.
Extended European Search Report for Application No. EP 19862819.0, dated Jun. 10, 2022, 11 pages.
Extended European Search Report for EP Application No. 20745781.3, dated Oct. 26, 2022, 8 Pages.
Extended European Search Report for European Application No. 17776639.1, dated Sep. 26, 2019, 8 pages.
(2016) History of Changes for Study: NCT02302157, https://clinicaltrials.gov/ct2/history/NCT02302157?v_17=View#StudyPageTop, 5 pages.
International Preliminary Report on Patentability for International Application No. PCT/US2017/051677, dated Mar. 28, 2019, 10 pages.
International Preliminary Report on Patentability for PCT Application No. PCT/US2017/24986, dated Oct. 11, 2018, 8 pages.
International Preliminary Report on Patentability received for PCT Application No. PCT/US2019/52015, dated Apr. 1, 20218, 16 pages.
International Search Report and Written Opinion for PCT Application No. PCT/US2017/24986, dated Aug. 22, 2017, 11 pages.
International Search Report and Written Opinion issued in International Application No. PCT/US2017/051677, dated Dec. 4, 2017, 11 pages.
International Search Report and Written Opinion received for International Application No. PCT/US19/52015, dated Apr. 14, 2020, 20 pages.
International Search Report and Written Opinion received for PCT Patent International Application No. PCT/US2022/014373, dated Jun. 30, 2022, 10 pages.
International Search Report and Written Opinion received for PCT Patent International Application No. PCT/US2022/019847, dated Jun. 27, 2022, 10 pages.
Alsanie et al. (2013) "Human Embryonic Stem Cell-Derived Oligodendrocytes: Protocols and Perspectives", Stem Cells and Development, 22(18):2459-2472.
Anderson et al. (Nov. 25, 2008) "Acceptable benefits and risks associated with surgically improving arm function in individuals living with cervical spinal cord injury", Spinal Cord, 47(4):334-338.
Bain et al. (Apr. 1995) "Embryonic Stem Cells Express Neuronal Properties in Vitro", Developmental Biology, 168:342-357.
Behrmann et al. (1992) "Spinal cord injury produced by consistent mechanical displacement of the cord in rats: behavioral and histologic analysis", Journal of Neurotrauma, 9(3):197-217.
Bian et al. (May 18, 2016) "Sequential Differentiation of Embryonic Stem Cells into Neural Epithelial-like Stem", Plos One, 11(5): 15 pages.
Cao et al. (Jan. 2001) "Pluripotent Stem Cells Engrated into the Normal or Lesioned Adult Rat Spinal Cord Are Restricted to a Glial Lineage", Experimental Neurology, 167(1):48-58.
Chapman et al. (Sep. 2012) "Evaluating the first-in-human clinical trial of a human embryonic stem cell-based therapy", Kennedy Institute of Ethics Journal, 22(3):243-261.
Davies et al. (Mar. 2, 2011) "Transplantation of Specific Human Astrocytes Promotes Functional Recovery after Spinal Cord Injury", Plos One, e17328, 6(3): 13 pages.
Doi et al. (Feb. 10, 2012) "Prolonged Maturation Culture Favors a Reduction in the Tumorigenicity and the Dopaminergic Function of Human ESC-Derived Neural Cells in a Primate Model of Parkinson's Disease", Stem cells, 30(5):935-945.
Douvaras et al. (Aug. 12, 2014) "Efficient Generation of Myelinating Oligodendrocytes from Primary Progressice Multiple Sclerosis Patients by Induced Pluripotent Stem Cells", Stem Cell Reports, 3(2):250-259.
Du et al. (2014) "Mechanism of SB431542 in Inhibiting Mouse Embryonic Stem Cell Differentiation", Cellular Signalling, 26(10):2107-2116.
Faulkner et al. (Dec. 2005) "Human Embryonic Stem Cell-Derived Oligodendrocyte Progenitors for the Treatment of Spinal Cord Injury", Transplant Immunology, 15(2):131-142.
Fuhrmann et al. (Jan. 1, 2016) "Injectable Hydrogel Promotes Early Survival of Induced Pluripotent Stem Cell-Derived Oligodendrocytes and Attenuates Longterm Teratoma Formation in a Spinal Cord Injury Model", Biomaterials, 83:23-36.
Goldman, Steven A. (Jul. 2005) "Stem and Progenitor Cell-based Therapy of the Human Central Nervous System", Nature Biotechnology, 23(7):862-871.
Gordon et al. (Jan. 2012) "Chemokines Influence the Migration and Fate of Neural Precursor Cells from the Young Adult and Middle-aged Rat Subventricular Zone", Experimental Neurology, 233(1):587-594.
Hatch et al. (2009) "Derivation of High-Purity Oligodendroglial Progenitors", Methods in Molecular Biology, 549:59-75.
Hu et al. (Oct. 15, 2009) "Differentiation of Human Oligodendrocytes from Pluripotent Stem Cells", Nature Protocols, 4(11):1614-1622.
Hu et al. (Sep.-Oct. 2009) "Hepatocyte growth factor enhances the generation of high-purity oligodendrocytes from human embryonic stem cells", Differentiation, 78(2-3):177-184.
Hulsebosch et al. (Jan. 29, 2009) "Rodent Model of Chronic Central Pain After Spinal Cord Contusion Injury and Effects of Gabapentin", Journal of Neurotrauma, 17(12):1205-1217.
Karimi-Abdolrezaee et al. (Mar. 29, 2006) "Delayed Transplantation of Adult Neural Precursor Cells Promotes Remyelination and Functional Neurological Recovery After Spinal Cord Injury", Journal of Neuroscience, 26(13):3377-3389.

(56) References Cited

OTHER PUBLICATIONS

Klimaschewski et al. (Nov. 2001) "Regulation of Clusterin Expression Following Spinal Cord Injury", Cell and Tissue Research, 306(2):209-216.

Kriks et al. (Nov. 6, 2011) "Dopamine Neurons Derived from Human ES Cells Efficiently Engraft In Animal Models of Parkinson's Disease", Nature, 480(7378):547-551.

Kuespert et al. (May 1, 2016) "Something 2 Talk About—Transcriptional Regulation in Embryonic And Adult Oligodendrocyte Precursors", Brain Research, 1638:16 pages.

Li et al. (May 15, 2013) "Differentiation of Oligodendrocyte Progenitor Cells From Human Embryonic Stem Cells On Vitronectin-Derived Synthetic Peptide Acrylate Surface", Stem Cells and Development, 22(10):1497-1505.

Lu et al. (2014) "Long-Distance Axonal Growth from Human Induced Pluripotent Stem Cells After Spinal Cord Injury", Neuron, 83(4):789-796.

Ma et al. (2009) "Oligodendrocyte Precursor Cells Differentially Expressing Noga-A but Not Mag Are More Permissive to Neurite Outgrowth Than Mature Oligodendrocytes", Experimental Neurology, 217(1):184-196.

Metz et al. (2000) "Validation of the Weight-Drop Contusion Model in Rats: A Comparative Study of Human Spinal Cord Injury", Journal of Neurotrauma, 17(1):1-17.

Mitsui et al. (2005) "Transplantation of Neuronal and Glial Restricted Precursors Into Contused Spinal Cord Improves Bladder and Motor Functions, Decreases Thermal Hypersensitivity, and Modifies Intraspinal Circuitry", Journal of Neuroscience, 25(42):9624-9636.

Nakamura et al. (Jun. 20, 2005) "Transplantation of Embryonic Spinal Cord-Derived Neurospheres Support Growth of Supraspinal Projections and Functional Recovery After Spinal Cord Injury in the Neonatal Rat", Journal of Neuroscience, 81(4):457-468.

Nemati et al. (2016) "Scalable Expansion of Human Pluripotent Stem Cell-Derived Neural Progenitors in Stirred Suspension Bioreactor Under Xeno-free Condition", Methods in Molecular Biology, 1502:143-58.

Noble et al. (2011) "Precursor Cell Biology and the Development of Astrocyte Transplantation Therapies: Lessons from Spinal Cord Injury", Neurotherapeutics, 8(4):677-693.

Nothias et al. (2005) "Combined Effects of Neurotrophin Secreting Transplants, Exercise, and Serotonergic Drug Challenge Improve Function In Spinal Rats", Neurorehabilitation and Neural Repair, 19(4):296-312.

Polisetti et al. (Jul. 11, 2017) "Laminin-511 and -521-Based Matrices for Efficient Ex Vivo-Expansion Of Human Limbal Epithelial Progenitor Cells", Scientific Reports, 5152, 7(1):15 pages.

Roy et al. (Oct. 22, 2006) "Functional Engraftment of Human ES Cell-Derived Dopaminergic Neurons Enriched by Coculture with Telomerase-Immortalized Midbrain Astrocytes", Nature Medicine, 12(11):1259-1268.

Scheff et al. (2003) "Experimental Modeling of Spinal Cord Injury: Characterization of a Force-Defined Injury Device", Journal of Neurotrauma, 20(2):179-193.

Sharp et al. (Jan. 2010) "Human Embryonic Stem Cell-Derived Oligodendrocyte Progenitor Cell Transplants Improve Recovery after Cervical Spinal Cord Injury", Stem Cells, 28(1):152-163.

Singh, Juhi (2018) "Role of PDGF-A Activated Intracellular Signalling in Oligodendrocyte Progenitor Migration", PhD Thesis, 153 pages.

Sokol, Sergei Y. (Oct. 2011) "Maintaining Embryonic Stem Cell Pluripotency with WNT Signaling", 138(20):4341-4350.

Sundberg et al. (2010) "Production and Isolation of NG2+ Oligodendrocyte Precursors from Human Embryonic Stem Cells in Defined Serum-Free Medium", Stem Cell Research, 5(2):91-103.

Tang et al. (2014) "Redirection of Doublecortin-Positive Cell Migration by OverExpression of the Chemokines MCP-1, MIP-1 a and Gro-a in the Adult Rat Brain", Neuroscience, 260:240-248.

Totiou et al. (2005) "Spinal Cord Injury is Accompanied by Chronic Progressive Demyelination", The journal of comparative neurology, 486:373-383.

Vadivelu et al. (2015) "Ng2+ Progenitors Derived from Embryonic Stem Cells Penetrate Glial Scar and Promote Axonal Outgrowth Into White Matter After Spinal Cord Injury", Stem Cells Translational Medicine, 4(4):401-411.

Wang et al. (2014) "ApoE Mimetic Ameliorates Motor Deficit and Tissue Damage in Rat Spinal Cord Injury", Journal of Neuroscience Research, 92(7):884-892.

Wirth, E. (May 16, 2014) "Phase I Clinical Trial of Human Embryonic Stem Cell-Derived Oligodendrocyte Progenitors in Subjects with Neurologically Complete Thoracic Spinal Cord Injury: Results and Next Steps", American Spinal Injury Association (ASIA) 2014 Meeting, San Antonio, Texas, (Oral Presentation), 7 pages.

Wright et al. (2014) "Novel Roles for Osteopontin and Clusterin in Peripheral Motor and Sensory Axon Regeneration", Journal of Neuroscience, 34(5):1689-1700.

Zhang et al. (Apr. 2011) "Role of Matrix Metalloproteinases and Therapeutic Benefits of Their Inhibition in Spinal Cord Injury", Neurotherapeutics, 8(2):206-220.

Kirkeby et al. (Jun. 28, 2012) "Generation of Regionally Specified Neural Progenitors And Functional Neurons From Human Embryonic Stem Cells Under Defined Conditions", Cell Reports, 1(6):703-714.

Nistor et al. (Feb. 2005) "Human Embryonic Stem Cells Differentiate into Oligodendrocytes In High Purity And Myelinate After Spinal Cord Transplantation", Glia, 49(3):385-396.

Zhang et al. (2006) "Oligodendrocyte Progenitor Cells Derived from Human Embryonic Stem Cells Express Neurotrophic Factors", Stem Cells and Development, 15(6):943-952.

\* cited by examiner

DORSALLY-DERIVED OLIGODENDROCYTE PROGENITOR CELLS FROM HUMAN PLURIPOTENT STEM CELLS

RELATED APPLICATIONS

This application claims priority to U.S. Provisional Application 62/796,077, filed Jan. 23, 2019, the entire contents of which are hereby incorporated by reference.

FIELD OF THE INVENTION

The present disclosure relates to novel methods for differentiating pluripotent stem cells such as human embryonic stem cells first to neuroectoderm progenitor cells with dorsal spinal cord progenitor phenotype, then further to glial progenitor cells, and further to oligodendrocyte progenitor cells. Also provided are cells and cellular compositions obtained by such methods, and uses of such cells. The present disclosure further relates to cells produced by the methods according to the invention that express one or more markers.

BACKGROUND OF THE INVENTION

Oligodendrocyte progenitor cells (OPCs) are a subtype of glial cells in the central nervous system (CNS) that arise in the ventricular zones of the brain and spinal cord and migrate throughout the developing CNS before maturing into oligodendrocytes. Mature oligodendrocytes produce the myelin sheath that insulates neuronal axons and remyelinate CNS lesions where the myelin sheath has been lost. Oligodendrocytes also contribute to neuroprotection through other mechanisms, including production of neurotrophic factors that promote neuronal survival (Wilkins et al., 2001 *Glia* 36(1):48-57; Dai et al., 2003 *J Neurosci.* 23(13):5846-53; Du and Dreyfus, 2002 *J Neurosci Res.* 68(6):647-54). Unlike most progenitor cells, OPCs remain abundant in the adult CNS where they retain the ability to generate new oligodendrocytes. Accordingly, OPCs and mature oligodendrocytes derived from OPCs are an important therapeutic target for demyelinating and dysmyelinating disorders (such as multiple sclerosis, adrenoleukodystrophy and adrenomyeloneuropathy), other neurodegenerative disorders (such as Alzheimer's disease, amyotrophic lateral sclerosis, and Huntington's disease) and acute neurological injuries (such as stroke and spinal cord injury (SCI)).

Several protocols have been developed for differentiation of human pluripotent stem cells such as embryonic stem cells (ESCs) and induced pluripotent stem cells (iPSCs) into OPCs that can be used in cellular therapy. To date, protocols for generating oligodendrocyte progenitor cells from human pluripotent stem cells have recapitulated the ventral motor neuron progenitor (pMN) domain of the developing spinal cord, which is known to give rise to the majority of spinal cord OPCs in vivo (Rowitch, 2004 *Nat Rev Neurosci.* 5(5):409-19; Ravanelli and Appel, 2015 *Genes Dev.* 29(23):2504-15). The induction of ventral neural progenitor cells that give rise to ventrally-derived OPCs requires activation of sonic hedgehog (SHE) signaling. (Ericson et al., 1996 *Cell* 87: 661-673; Orentas et al., 1999 *Development* 126 (11):2419-29). Consequently, existing in vitro protocols for production of OPCs from pluripotent stem cells rely on either embryoid body formation as a means to stimulate endogenous SHE activation (Nistor et al., 2005 *Glia* 49(3):385-96) or direct addition of SHH or an activator of SHH signaling (Stacpoole et al., 2013 *Stem Cell Reports* 1(5):437-50; Douvaras and Fossati, 2015 *Nat Protoc.* 10(8):1143-54; Piao et al., 2015 *Cell Stem Cell* 16(2):198-210; Wang et al., 2013 *Cell Stem Cell* 12(2):252-64; Rodrigues et al., 2017 *Stem Cell Reports* 8(6):1770-1783; and Yamashita et al., 2017 *PLoS One* 12(2):e0171947). The former approach can be problematic because it relies on spontaneous differentiation within the embryoid bodies and can result in unwanted cell types at the end of the differentiation process (Priest et al., 2015 *Regen Med.* 10(8):939-58; Manley et al., 2017 *Stem Cells Transl Med.* 6(10):1917-1929). The latter directed differentiation represent the current approaches for production of pluripotent stem cell-derived OPCs. While these methods have been successful in generating OPCs from human pluripotent stem cells for research purposes, challenges remain with respect to quality, scalability and cost of goods associated with translating the existing protocols to a clinical commercial-scale production process.

In the mouse, a smaller secondary wave of OPCs are generated in the dorsal spinal cord independent of SHE signaling (Cai et al., 2005 *Neuron* 45(1): 41-53; Vallstedt et al., 2005 *Neuron* 45(1): 55-67). These dorsally-derived mouse OPCs mature into oligodendrocytes that contribute to axonal myelination during development and remyelination in response to a focal myelination injury (Zhu et al., 2011 *Glia* 59(11):1612-21). Much less is known about putative dorsally-derived OPC populations in the human. Recently, it was reported that human brain region-specific forebrain organoids (dorsal forebrain organoids and ventral forebrain organoids) consisting of multiple cell types and generated using OLIG2-GFP knock-in hPSC reporter lines can be differentiated into both functional neurons and oligodendroglial cells (Kim et al., available at https://www.biorxiv.org/content/biorxiv/early/2018/11/04/460907.full.pdf). However, to date, there have been no reports of dorsally-derived OPCs obtained by a directed differentiation of human pluripotent stem cells that can give rise to a targeted lineage-specific cell population suitable for downstream cellular therapy applications.

There is a need for improved methods for differentiating pluripotent stem cells into OPCs. Ideally, such methods should be easily scalable to produce sufficient quantities of OPCs for cell therapy applications while consistently and reproducibly producing the targeted cell OPCs with the desired quality attributes.

SUMMARY OF THE INVENTION

In various embodiments described herein, the present disclosure provides, inter alia, robust, reliable protocols for differentiating human pluripotent stem cells such as ESCs and iPSCs into dorsal neuroectoderm progenitor cells (dNPCs) and further to glial progenitor cells and OPCs.

The present disclosure is based, in part, on the discovery that human pluripotent stem cells can be readily and efficiently differentiated into spinal cord OPCs in the absence of ventralization of neuroectoderm-restricted progenitor cells mediated by SHH signaling.

In certain aspects of the present disclosure, neuroectoderm precursor cells with a dorsal spinal cord phenotype are obtained by contacting human pluripotent stem cells with one or more inhibitors of mitogen-activated protein kinase/extracellular signal regulated kinase (MAPK/ERK) signaling combined with one or more inhibitors of bone morphogenic protein (BMP) signaling and retinoic acid. This approach is in contrast with current methods of inducing neuroectoderm that rely on the combined addition of a transforming growth factor beta (TGFβ)/Activin/Nodal signaling inhibitor together with a BMP signaling inhibitor, also known as dual SMAD inhibition (Chambers et al., 2009 *Nat. Biotechnol* 27 (3):275-280; Douvaras and Fossati, 2015 *Nat Protoc.* 10(8):1143-54; Piao et al., 2015 *Cell Stem Cell* 16(2)).

Surprisingly, it was discovered that the dorsal neuroectoderm progenitors obtained according to the above protocol and not exposed to the ventralizing morphogen SHH or a SHH signaling activator, could be readily differentiated to spinal cord OPCs. It was also discovered that in comparison to differentiation protocols where SHH signaling is activated, the methods of the present disclosure yielded a significantly larger number of differentiated cells. Due to the substantial increase in cell expansion and cell yield, the methods of the present disclosure provide scalable and reproducible processes to produce large quantities of OPCs and other neuroectoderm lineage cells for cell therapy and other applications.

The methods of the present disclosure reproducibly produce neuroectoderm progenitor cells with a dorsal spinal cord phenotype by day 7 of the differentiation process, glial progenitor cells by day 21 of the differentiation process and OPCs by day 42 of the differentiation process. The Day 42 OPCs produced in accordance with the present disclosure are comparable (in terms of their overall marker expression profile) to OPCs generated using an alternative method that are currently in clinical testing to treat spinal cord injury (Priest et al., 2015 *Regen Med.* 10(8):939-58; Manley et al., 2017 *Stem Cells Transl Med.* 6(10):1917-1929), with the exception that the OPCs produced in accordance with present disclosure express lower levels of non-OPC markers, including markers associated with epithelial cyst formation in vitro.

In a preferred embodiment, the OPCs produced according to the methods of the invention express one or more markers selected from neural/glial antigen 2 (NG2), platelet-derived growth factor receptor A (PDGFRα) and ganglioside GD3 (GD3). In a further preferred embodiment, the cells can be characterized by expression of a single marker or a combination of markers. For example, the OPCs produced according to the methods of the invention can be characterized solely by NG2, PDGFRα, or GD3, or combinations of markers with two or three of markers NG2, PDGFRα, and GD3. In one preferred embodiment, at least 90% of the cells produced according to the methods of the invention express NG2 and/or PDGFRα. In a further preferred embodiment, at least 50% of the cells further express GD3.

In a further preferred embodiment, the process of producing the cells involves one or more steps of cryopreserving cells into an intermediate bank and then thawing the cells to continue with the differentiation process up to the final product. For example, an intermediate cell bank can be cryopreserved on day 14, day 28 and/or day 35 of the process.

In another embodiment, the OPCs produced according to the invention are prepared as a ready to administer (RTA) OPC cell therapy composition for the treatment of a patient. A method of formulating human OPCs for administration to a subject directly after thawing and of formulating OPC cell therapy compositions for cryopreservation and the administration of the cryopreserved composition to a subject subsequent to thawing are also presented. In another aspect, the RTA composition may be formulated as a thaw and inject (TAI) composition, whereby the composition is administered by injection subsequent to thawing, without further processing of the OPCs.

In one embodiment, the present disclosure provides a method of obtaining a population of cells comprising dorsal neural progenitor cells (dNPCs) from undifferentiated human pluripotent stem cells. In certain embodiments, the method comprises: a) obtaining a culture of undifferentiated human pluripotent stem cells; b) culturing the undifferentiated human pluripotent stem cells adherently in the presence of at least one inhibitor of mitogen-activated protein kinase/extracellular signal-regulated kinase (MAPK/ERK), at least one inhibitor of bone morphogenetic protein (BMP) signaling and retinoic acid for a first time period, thereby inducing differentiation to neuroectoderm; and c) culturing the cells from b) adherently in the presence of retinoic acid and in the absence of sonic hedgehog (SHH) or a SHH signaling activator for a second time period, thereby obtaining dorsal neural progenitor cells.

In certain embodiments, the first time period is about three to four days. In certain embodiments, the second time period is about three to four days.

In certain embodiments, the method further comprises an additional step of harvesting the cells from step c), replating the harvested cells on a substrate and further culturing the cells adherently in the presence of basic fibroblast growth factor (bFGF) and epidermal growth factor (EGF) for a further time period, thereby expanding the cells. In certain embodiments, the substrate is a cell adhesion peptide. In other embodiments, the substrate is an extracellular matrix protein. In certain embodiments, the substrate is recombinant human laminin-521. In other embodiments, the substrate is vitronectin or laminin-511 E8 fragment. In yet other embodiments, the substrate is a synthetic substrate, such as, for example, Synthemax®-II SC Substrate.

In further embodiments, the method comprises an additional step of harvesting the expanded cells and culturing them as aggregates in suspension in the presence of bFGF and EGF for a further time period, until the cells have matured into glial progenitor cells. In certain embodiments, the culturing is performed in dynamic suspension. In certain embodiments, the cells are cultured in suspension for about five to ten days. In an embodiment, the cells are cultured in suspension for about seven days.

In yet further embodiments, the method comprises an additional step of plating down the aggregates comprising glial progenitor cells on a substrate and culturing the cells adherently for a further time period in the presence of epidermal growth factor (EGF), optionally splitting the cells from time to time, until the cells have matured into oligodendrocyte progenitor cells (OPCs). In certain embodiments, the culture medium additionally comprises platelet-derived growth factor AA (PDGF-AA). In certain embodiments, the cells are cultured for about two to four weeks after the plate-down of the aggregates comprising glial progenitor cells. In an embodiment, the cells are cultured for twenty-one days after the plate-down of the aggregates comprising glial progenitor cells. In certain embodiments, the substrate is a cell adhesion peptide. In other embodiments, the substrate is an extracellular matrix protein. In certain embodiments, the substrate is recombinant human laminin-521. In other embodiments, the substrate is vitronectin or laminin-511 E8 fragment. In yet other embodiments, the substrate is a synthetic substrate, such as, for example, Synthemax®-II SC Substrate.

In another embodiment, cells are cultured without coating in some parts of the process. In another embodiment, coated or uncoated microcarriers in suspension are used instead of a culture dish.

In certain embodiments, the at least one inhibitor of MAPK/ERK is selected from the group consisting of PD0325901, AZD6244, GSK1120212, PD184352 and Cobimetinib. In yet other embodiments, the inhibitor of MAPK/ERK is PD0325901.

In certain embodiments, the at least one inhibitor of BMP signaling is an inhibitor of activin receptor-like kinase 2 (ALK2). In certain embodiments, the at least one inhibitor of BMP signaling is selected from the group consisting of Dorsomorphin, DMH-1, K02288, ML347, LDN193189 and Noggin protein. In yet other embodiments, the inhibitor of BMP signaling is Dorsomorphin.

An additional embodiment is a differentiated cell population comprising paired box 6 (PAX6) positive dorsal neural progenitor cells (dNPCs) obtained in accordance with the present disclosure. In certain embodiments, the PAX6 positive dNPCs further express one or more markers selected from paired box 3 (PAX3), paired box 7 (PAX7) and activating protein 2 (AP2).

In another embodiment, the present disclosure provides a method of obtaining a population of cells comprising neural/glial antigen 2 (NG2) positive oligodendrocyte progenitor cells (OPCs) from undifferentiated human pluripotent stem cells, the method comprising: a) obtaining a culture of undifferentiated human pluripotent stem cells; b) culturing the undifferentiated human pluripotent stem cells adherently in the presence of at least one inhibitor of mitogen-activated protein kinase/extracellular signal-regulated kinase (MAPK/ERK) signaling, at least one inhibitor of bone morphogenetic protein (BMP) signaling and retinoic acid for a first time period, thereby inducing differentiation to neuroectoderm; c) culturing the cells from b) adherently in the presence of retinoic acid and in the absence of sonic hedgehog (SHH) or a SHH signaling activator for a second time period, thereby obtaining dorsal neural progenitor cells; d) harvesting the cells from c), replating them on a substrate and culturing the cells adherently in the presence of basic fibroblast growth factor (bFGF) and epidermal growth factor (EGF) for a further time period, thereby expanding the neural progenitor cells; e) harvesting the cells from d) and further culturing the cells as aggregates in suspension in the presence of bFGF and EGF for a further time period, until the cells have matured into dorsal glial progenitor cells; and f) plating down the aggregates from e) on a substrate and culturing the cells adherently for a further time period in the presence of epidermal growth factor (EGF), optionally splitting the cells from time to time, until the cells have matured into OPCs. In certain embodiments, the culture medium in step f) additionally comprises platelet-derived growth factor AA (PDGF-AA). In certain embodiments, the cells are cultured for about two to four weeks after the plate-down of the aggregates. In an embodiment, the cells are cultured for about twenty-one days after the plate-down of the aggregates. In certain embodiments, the substrate is a cell adhesion peptide. In other embodiments, the substrate is an extracellular matrix protein. In certain embodiments, the substrate is recombinant human laminin-521. In other embodiments, the substrate is vitronectin or laminin-511 E8 fragment. In yet other embodiments, the substrate is a synthetic substrate, such as, for example, Synthemax®-II SC Substrate.

An additional embodiment is a differentiated cell population comprising NG2 positive OPCs obtained in accordance with the present disclosure. In certain embodiments, the differentiated cell population comprises at least 60% of cells that are NG2 positive. In certain embodiments, the differentiated cell population comprises at least 70% of cells that are NG2 positive. In certain embodiments, the differentiated cell population comprises at least 80% of cells that are NG2 positive. In other embodiments, the differentiated cell population comprises at least 90% of cells that are NG2 positive. In certain embodiments, the differentiated cell population comprises at least 98% of cells that are NG2 positive.

In certain embodiments, the differentiated cell population comprises at least 60% of cells that are PDGFRα positive. In certain embodiments, the differentiated cell population comprises at least 70% of cells that are PDGFRα positive. In certain embodiments, the differentiated cell population comprises at least 80% of cells that are PDGFRα positive. In other embodiments, the differentiated cell population comprises at least 90% of cells that are PDGFRα positive. In certain embodiments, the differentiated cell population comprises at least 98% of cells that are PDGFRα positive.

In certain embodiments, the differentiated cell population comprises at least 50% of cells that are GD3 positive. In certain embodiments, the differentiated cell population comprises at least 60% of cells that are GD3 positive. In certain embodiments, the differentiated cell population comprises at least 70% of cells that are GD3 positive. In certain embodiments, the differentiated cell population comprises at least 80% of cells that are GD3 positive. In other embodiments, the differentiated cell population comprises at least 90% of cells that are GD3 positive. In certain embodiments, the differentiated cell population comprises at least 98% of cells that are GD3 positive.

In another embodiment, the differentiated cell population comprises cells that are NG2 and PDGFRα positive within the percentages mentioned above. In another embodiment, the differentiated cell population comprises cells that are NG2 and GD3 positive within the percentages mentioned above. In another embodiment, the differentiated cell population comprises cells that are PDGFRα and GD3 positive within the percentages mentioned above. In another embodiment, the differentiated cell population comprises cells that are NG2, PDGFRα, and GD3 positive within the percentages mentioned above.

In certain embodiments, the human pluripotent stem cells are human embryonic stem cells. In other embodiments, the human pluripotent stem cells are human induced pluripotent stem cells.

In another embodiment, the cells prepared according to the invention are cryopreserved, and then subsequently thawed for delivery to the patient. In a preferred embodiment, the cells need no further processing before delivery to the patient. Once thawed, the cells prepared according to the invention may be immediately delivered to the patient. In a preferred embodiment, the cells may be delivered by injection. The volume of the injection may be, for example about 100 microliters, with a cell concentration of 100,000,000 live cells per ml.

BRIEF DESCRIPTION OF THE DRAWINGS

FIG. 2A shows Day 7 to Day 14 yield across multiple different combinations of small molecule treatment that were tested. "+PMA" and "−PMA" refer to the presence or absence of SHH agonist Purmorphamine during Days 4-6 of the differentiation process, respectively. Black bars for Condition A, Condition B, and Condition E correspond to neuroectoderm cells that were derived using a differentiation cocktail comprising the MAPK/ERK inhibitor PD0325901, the BMP inhibitor Dorsomorphin and retinoic acid, whereas grey bars for Condition C, Condition D, and Condition F correspond to neuroectoderm cells derived using other signaling modulators. FIG. 2B shows step yields for various time points of two representative runs (Run 1 and Run 2) in accordance with the differentiation protocol disclosed in the present disclosure compared with a differentiation process which included PMA (Prior Process (+PMA)). FIG. 2C depicts overall theoretical yield from one uhESC for two representative runs (Run1 and Run 2) in accordance with the present disclosure and compared against a differentiation process which included PMA (Prior Process (+PMA)).

DETAILED DESCRIPTION OF THE INVENTION

Figure 1:
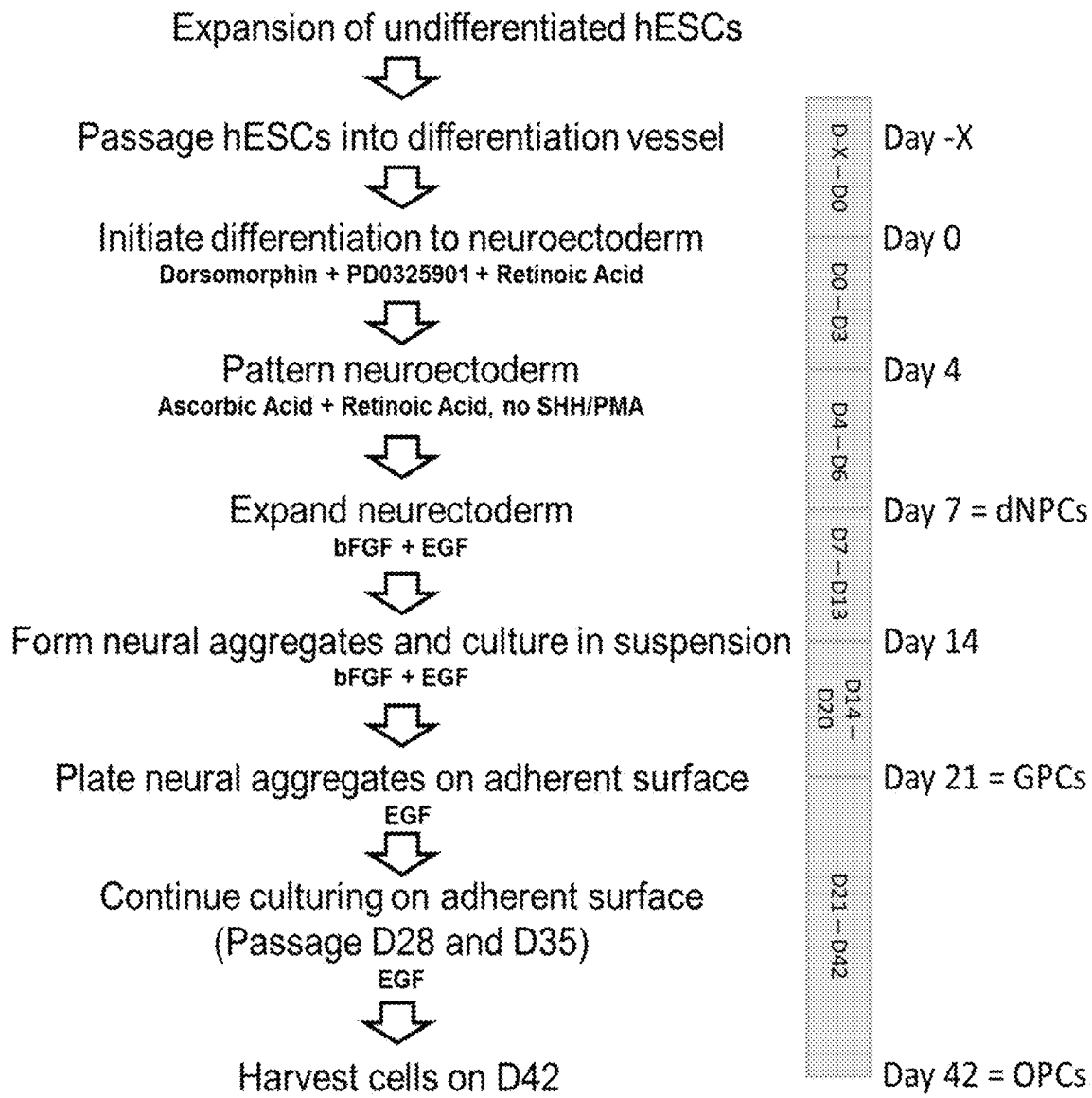
FIG. 1 is a diagram depicting differentiation of human pluripotent stem cells to dorsal neuroectoderm progenitor cells (dNPCs) and further to glial progenitor cells (GPCs) and oligodendrocyte progenitor cells (OPCs) in accordance with the present disclosure. Neuroectoderm progenitor cells with a dorsal spinal cord phenotype are obtained around day 7, and can be readily differentiated to GPCs (day 21) and further to OPCs (day 42). Several additional small molecule inhibitors of MAPK/ERK signaling (other than PD0325901) and BMP signaling (other than Dorsomorphin) were tested and were found to work equally well in the induction of differentiation to dorsal neuroectoderm (Example 7).

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to affect a disavowal of any part of the full scope of the invention. Hence, the following descriptions are intended to illustrate some particular aspects of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents and other references cited herein are incorporated by reference in their entireties.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

Methods disclosed herein can comprise one or more steps or actions for achieving the described method. The method steps and/or actions may be interchanged with one another without departing from the scope of the present invention. In other words, unless a specific order of steps or actions is required for proper operation of the aspect, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a percentages, density, volume and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, "oligodendrocyte progenitor cells" (OPCs) refer to cells found in the central nervous system that are of a neuroectoderm/glial lineage, express the characteristic marker neural/glial antigen 2 (NG2) and are capable of differentiating into oligodendrocytes.

The terms "glial lineage cells," "glial progenitor cells" and "glial cells" are used interchangeably herein and refer to non-neuronal CNS cells that are derived from neuroectoderm/neural progenitor cells. Glial progenitor cells can be further differentiated to form OPCs/oligodendrocytes or astrocytes. In certain embodiments, the glial progenitor cells of the present disclosure express one or more markers selected from calcium voltage-gated channel auxiliary subunit gamma 4 (CACNG4), fatty acid binding protein 7 (FABP7), and netrin-1 receptor (DCC).

The terms "neuroectoderm," "neuroectoderm cells," "neuroectoderm precursor," "neuroectoderm progenitor," "neural progenitor" and "neural precursor" are used interchangeably herein and refer to cells that can be differentiated along a neural precursor pathway and that are capable of forming CNS neurons, oligodendrocytes, astrocytes and ependymal cells. In certain embodiments, the neuroectoderm cells of the present disclosure express one or more markers selected from paired box 6 (PAX6), Hes family BHLH transcription factor 5 (HESS) and zinc finger and BTB domain containing 16 (ZBTB16).

As used herein, the terms "dorsal" and "ventral" refer to distinct neural cell subtypes emerging from progenitor cells arrayed into spatially discrete domains along the dorsal-ventral axis of the neural tube in the developing spinal cord. This process, known as dorsal-ventral patterning, is controlled by secreted signals that partition the neural progenitor cells. BMP and Wnt signaling initiate patterning from the dorsal neural tube (Lee and Jessell, 1999 *Annu. Rev. Neurosci.* 22: 261-294), whereas secretion of SHH has a key role in establishing ventral neuronal cell fates (Chiang et al., 1996 *Nature* 383: 407-413; Ericson et al., 1996 Cell 87: 661-683; Briscoe et al., 2001 *Mol. Cell* 7:1279-1291).

The terms "dorsal neuroectoderm progenitor cell," "dorsal neural progenitor cell" and "dNPC" are used interchangeably herein and refer to a neural progenitor cell that has the dorsal spinal cord phenotype and has been obtained by differentiating pluripotent stem cells to neuroectoderm-restricted precursors in the absence of exogenous SHH or a SHH signaling activator. In certain embodiments, the dNPCs express one or more markers selected from paired box 3 (PAX3), paired box 7 (PAX7) and activating protein 2 (AP2).

As used herein, the term "embryoid body" (EB) refers to a three-dimensional cellular aggregate derived from pluripotent stem cells that has undergone spontaneous differentiation towards all three germ layers. EBs are formed when pluripotent stem cells are removed from culture conditions that inhibit differentiation. For example, in the case of human embryonic stem cells, removal of basic fibroblast growth factor (bFGF) and transforming growth factor beta (TGFβ) from the culture media results in spontaneous differentiation towards all three germ layers and formation of EBs.

As used herein, the term "BMP signaling inhibitor" refers to a small molecule or protein modulator that is capable of downregulating signaling along the bone morphogenetic protein (BMP) signaling pathway. In certain embodiments, the BMP signaling inhibitor directly targets Activin A receptor, type I (ACVR1), also known as activin receptor-like kinase 2 (ALK2). In certain embodiments, the BMP signaling inhibitor is selected from the group consisting of Dorsomorphin, DMH-1, K02288, ML347, LDN193189 and Noggin protein.

As used herein, the term "MAPK/ERK inhibitor" refers to a small molecule or protein modulator that inhibits the MAPK/ERK kinase. In certain embodiments, the MAPK/ERK inhibitor is selected from the group consisting of PD0325901, AZD6244, GSK1120212, PD184352 and Cobimetinib.

The terms "SHH signaling activator," "SHH signaling agonist," "SHH activator" and "SHH agonist" are used interchangeably herein and refer to a small molecule or protein modulator that is capable of activating the Sonic Hedgehog (SHE) signaling pathway. Non-limiting examples of a SHE signaling activator include Purmorphamine (PMA), Smoothened Agonist (SAG, CAS 364590-63-6) and Sonic Hedgehog (SHE) protein.

As used herein, the term "undesirable cell types" refers to cells outside of the neuroectoderm lineage that can result in the formation of ectopic tissues upon implantation, or that result in the formation of one or more cysts in a cyst assay, as described herein. In an embodiment, "undesirable cell types" can include epithelial lineage cells such as cells positive for CD49f, a marker expressed by both neural progenitor cells and epithelial cells, or cells positive for CLDN6 or EpCAM, two markers expressed by both pluripotent cells and epithelial cells.

As used herein, "implantation" or "transplantation" refers to the administration of a cell population into a target tissue using a suitable delivery technique, (e.g., using an injection device).

As used herein, a "subject" refers to an animal or a human.

As used herein, a "subject in need thereof" refers to an animal or a human having damaged tissue in the central nervous system. In an embodiment, an animal or a human is experiencing a loss of motor function.

The terms "central nervous system" and "CNS" are used interchangeably herein and refer to the complex of nerve tissues that control one or more activities of the body, which include but are not limited to, the brain and the spinal cord in vertebrates.

As used herein, "treatment" or "treating," with respect to a condition or a disease, is an approach for obtaining beneficial or desired results including preferably clinical results after a condition or a disease manifests in a patient. Beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, prolonging survival, and any combination thereof. Likewise, for purposes of this disclosure, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, prolonging survival, and any combination thereof.

Propagation and Culture of Undifferentiated Pluripotent Stem Cells

Differentiation of pluripotent stem cells in accordance with the present disclosure can be carried out using any suitable pluripotent stem cells as a starting material. In one embodiment, a method can be carried out on an human embryonic stem cell (hESC) line. In another embodiment, a method can be carried out using induced pluripotent stem cells (iPSCs). In another embodiment, a method can be carried out using cells that are derived from an H1, H7, H9, H13, or H14 cell line. In another embodiment, a method can be carried out on a primate pluripotent stem (pPS) cell line.

In yet another embodiment, a method can be carried using undifferentiated stem cells derived from parthenotes, which are embryos stimulated to produce hESCs without fertilization.

Methods of propagation and culture of undifferentiated pluripotent stem cells have been previously described. With respect to tissue and cell culture of pluripotent stem cells, the reader may wish to refer to any of numerous publications available in the art, e.g., *Teratocarcinomas and Embryonic Stem cells: A Practical Approach* (E. J. Robertson, Ed., IRL Press Ltd. 1987); *Guide to Techniques in Mouse Development* (P. M. Wasserman et al., Eds., Academic Press 1993); *Embryonic Stem Cell Differentiation in Vitro* (M. V. Wiles, Meth. Enzymol. 225:900, 1993); *Properties and Uses of Embryonic Stem Cells: Prospects for Application to Human Biology and Gene Therapy* (P. D. Rathjen et al., Reprod. Fertil. Dev. 10:31, 1998; and R. I. Freshney, Culture of Animal Cells, Wiley-Liss, New York, 2000).

Undifferentiated pluripotent stem cells can be maintained in an undifferentiated state without added feeder cells (see, e.g., (2004) Rosler et al., *Dev. Dynam.* 229:259). Feeder-free cultures are typically supported by a nutrient medium containing factors that promote proliferation of the cells without differentiation (see, e.g., U.S. Pat. No. 6,800,480). In one embodiment, conditioned media containing such factors can be used. Conditioned media can be obtained by culturing the media with cells secreting such factors. Suitable cells include, but are not limited to, irradiated (~4,000 Rad) primary mouse embryonic fibroblasts, telomerized mouse fibroblasts, or fibroblast-like cells derived from pPS cells (U.S. Pat. No. 6,642,048). Medium can be conditioned by plating the feeders in a serum free medium, such as knockout DMEM supplemented with 20% serum replacement and 4 ng/mL bFGF. Medium that has been conditioned for 1-2 days can be supplemented with further bFGF, and used to support pPS cell culture for 1-2 days (see. e.g., WO 01/51616; Xu et al., (2001) *Nat. Biotechnol.* 19:971).

Alternatively, fresh or non-conditioned medium can be used, which has been supplemented with added factors (like a fibroblast growth factor or forskolin) that promote proliferation of the cells in an undifferentiated form. Non-limiting examples include a base medium like X-VIVO™ 10 (Lonza, Walkersville, Md.) or QBSF™-60 (Quality Biological Inc. Gaithersburg, Md.), supplemented with bFGF at 40-80 ng/mL, and optionally containing SCF (15 ng/mL), or Flt3 ligand (75 ng/mL) (see, e.g., Xu et al., (2005) *Stem Cells* 23(3):315). These media formulations have the advantage of supporting cell growth at 2-3 times the rate in other systems (see, e.g., WO 03/020920). In one embodiment, undifferentiated pluripotent cells such as hES cells, can be cultured in a media comprising bFGF and TGFβ. Non-limiting example concentrations of bFGF include about 80 ng/ml. Non-limiting example concentrations of TGFβ include about 0.5 ng/ml. In yet another embodiment, undifferentiated pluripotent stem cells can be maintained in a commercially available, complete medium such as mTeSR™ (Stem Cell Technologies, Vancouver, Canada).

Undifferentiated pluripotent cells can be cultured on a layer of feeder cells, typically fibroblasts derived from embryonic or fetal tissue (Thomson et al. (1998) *Science* 282:1145). Feeder cells can be derived from a human or a murine source. Human feeder cells can be isolated from various human tissues, or can be derived via differentiation of human embryonic stem cells into fibroblast cells (see, e.g., WO 01/51616). Human feeder cells that can be used include, but are not limited to, placental fibroblasts (see, e.g., Genbacev et al. (2005) *Fertil. Steril.* 83(5):1517), fallopian tube epithelial cells (see, e.g., Richards et al. (2002)*Nat. Biotechnol.*, 20:933), foreskin fibroblasts (see, e.g., Amit et al. (2003) *Biol. Reprod.* 68:2150), and uterine endometrial cells (see, e.g., Lee et al. (2005) *Biol. Reprod.* 72(1):42).

Various solid surfaces can be used in the culturing of undifferentiated pluripotent cells. Those solid surfaces include, but are not limited to, standard commercially available tissue culture flasks or cell culture plates, such as 6-well, 24-well, 96-well, or 144-well plates. Other solid surfaces include, but are not limited to, microcarriers and disks. Solid surfaces suitable for growing undifferentiated pluripotent cells can be made of a variety of substances including, but not limited to, glass or plastic such as polystyrene, polyvinylchloride, polycarbonate, polytetrafluorethylene, melinex, thermanox, or combinations thereof. Suitable surfaces can comprise one or more polymers, such as, e.g., one or more acrylates. A solid surface can be three-dimensional in shape. Non-limiting examples of three-dimensional solid surfaces have been previously described, e.g., in U.S. Patent Pub. No. 2005/0031598.

Undifferentiated stem cells can also be grown under feeder-free conditions on a growth substrate. A growth substrate can be a Matrigel® matrix (e.g., Matrigel®, Matrigel® GFR), recombinant laminin, laminin-511 recombinant fragment E8 or vitronectin. In certain embodiments of the present disclosure, the growth substrate is recombinant human laminin-521 (Biolamina, Sweden, distributed by Corning Inc., Corning, N.Y.). In other embodiments, the substrate is a synthetic substrate, such as, for example, Synthemax®-II SC Substrate.

Undifferentiated stem cells can be passaged or subcultured using various methods such as using collagenase, or such as manual scraping. Undifferentiated stem cells can be subcultured by enzymatic means that generate a single cell suspension, such as using Accutase® (distributed by Sigma Aldrich, Mo.) or similar trypsinases. Alternatively, undifferentiated stem cells can be subcultured using non-enzymatic means, such as 0.5 mM EDTA in PBS, or such as using ReLeSR™ (Stem Cell Technologies, Vancouver, Canada).

In an embodiment, a plurality of undifferentiated stem cells are seeded or subcultured at a seeding density that allows the cells to reach confluence in about three to about ten days. In an embodiment, the seeding density can range from about $6.0 \times 10^3$ cells/cm$^2$ to about $5.0 \times 10^5$ cells/cm$^2$, such as about $1.0 \times 10^4$ cells/cm$^2$, such as about $5.0 \times 10^4$ cells/cm$^2$, such as about $1.0 \times 10^5$ cells/cm$^2$, or such as about $3.0 \times 10^5$ cells/cm$^2$ of growth surface. In another embodiment, the seeding density can range from about $6.0 \times 10^3$ cells/cm$^2$ to about $1.0 \times 10^4$ cells/cm$^2$ of growth surface, such as about $6.0 \times 10^3$ cells/cm$^2$ to about $9.0 \times 10^3$ cells/cm$^2$, such as about $7.0 \times 10^3$ cells/cm$^2$ to about $1.0 \times 10^4$ cells/cm$^2$, such as about $7.0 \times 10^3$ cells/cm$^2$ to about $9.0 \times 10^3$ cells/cm$^2$, or such as about $7.0 \times 10^3$ cells/cm$^2$ to about $8.0 \times 10^3$ cells/cm$^2$ of growth surface. In yet another embodiment, the seeding density can range from about $1.0 \times 10^4$ cells/cm$^2$ to about $1.0 \times 10^5$ cells/cm$^2$ of growth surface, such as about $2.0 \times 10^4$ cells/cm$^2$ to about $9.0 \times 10^4$ cells/cm$^2$, such as about $3.0 \times 10^4$ cells/cm$^2$ to about $8.0 \times 10^4$ cells/cm$^2$, such as about $4.0 \times 10^4$ cells/cm$^2$ to about $7.0 \times 10^4$ cells/cm$^2$, or such as about $5.0 \times 10^4$ cells/cm$^2$ to about $6.0 \times 10^4$ cells/cm$^2$ of growth surface. In an embodiment, the seeding density can range from about $1.0 \times 10^5$ cells/cm$^2$ to about $5.0 \times 10^5$ cells/cm$^2$ of growth surface, such as about $1.0 \times 10^5$ cells/cm$^2$ to about $4.5 \times 10^5$ cells/cm$^2$, such as about $1.5 \times 10^5$ cells/cm$^2$ to about $4.0 \times 10^5$ cells/cm$^2$, such as about $2.0 \times 10^5$ cells/cm$^2$ to about $3.5 \times 10^5$ cells/cm$^2$, or such as about $2.5 \times 10^5$ cells/cm$^2$ to about $3.0 \times 10^5$ cells/cm$^2$ of growth surface.

Any of a variety of suitable cell culture and sub-culturing techniques can be used to culture stem cells in accordance with the methods of the present disclosure. For example, a culture medium can be completely exchanged daily, initiating about 2 days after sub-culturing of the cells. In an embodiment, when a culture reaches about 90% colony coverage, cells can be detached and seeded for subsequent culture using one or more suitable reagents, such as, e.g., Accutase® to achieve a single cell suspension for quantification. In an embodiment, undifferentiated stem cells can then be sub-cultured before seeding the cells on a suitable growth substrate (e.g., recombinant human laminin-521) at a seeding density that allows the cells to reach confluence over a suitable period of time, such as, e.g., in about three to ten days. In one embodiment, undifferentiated stem cells can be subcultured using Collagenase IV and expanded on a recombinant laminin. In another embodiment, undifferentiated stem cells can be subcultured using Collagenase IV and expanded on a Matrigel®. In one embodiment, undifferentiated stem cells can be subcultured using ReLeSR™ and expanded on recombinant human laminin-521.

For seeding undifferentiated stem cells, the seeding density can range from about $6.0 \times 10^3$ cells/cm$^2$ to about $5.0 \times 10^5$ cells/cm$^2$, such as about $1.0 \times 10^4$ cells/cm$^2$, such as about $5.0 \times 10^4$ cells/cm$^2$, such as about $1.0 \times 10^5$ cells/cm$^2$, or such as about $3.0 \times 10^5$ cells/cm$^2$ of growth surface. In another embodiment, the seeding density can range from about $6.0 \times 10^3$ cells/cm$^2$ to about $1.0 \times 10^4$ cells/cm$^2$ of growth surface, such as about $6.0 \times 10^3$ cells/cm$^2$ to about $9.0 \times 10^3$ cells/cm$^2$, such as about $7.0 \times 10^3$ cells/cm$^2$ to about $1.0 \times 10^4$ cells/cm$^2$, such as about $7.0 \times 10^3$ cells/cm$^2$ to about $9.0 \times 10^3$ cells/cm$^2$, or such as about $7.0 \times 10^3$ cells/cm$^2$ to about $8.0 \times 10^3$ cells/cm$^2$ of growth surface. In yet another embodiment, the seeding density can range from about $1.0 \times 10^4$ cells/cm$^2$ to about $1.0 \times 10^5$ cells/cm$^2$ of growth surface, such as about $2.0 \times 10^4$ cells/cm$^2$ to about $9.0 \times 10^4$ cells/cm$^2$, such as about $3.0 \times 10^4$ cells/cm$^2$ to about $8.0 \times 10^4$ cells/cm$^2$, such as about $4.0 \times 10^4$ cells/cm$^2$ to about $7.0 \times 10^4$ cells/cm$^2$, or such as about $5.0 \times 10^4$ cells/cm$^2$ to about $6.0 \times 10^4$ cells/cm$^2$ of growth surface. In an embodiment, the seeding density can range from about $1.0 \times 10^5$ cells/cm$^2$ to about $5.0 \times 10^5$ cells/cm$^2$ of growth surface, such as about $1.0 \times 10^5$ cells/cm$^2$ to about $4.5 \times 10^5$ cells/cm$^2$, such as about $1.5 \times 10^5$ cells/cm$^2$ to about $4.0 \times 10^5$ cells/cm$^2$, such as about $2.0 \times 10^5$ cells/cm$^2$ to about $3.5 \times 10^5$ cells/cm$^2$, or such as about $2.5 \times 10^5$ cells/cm$^2$ to about $3.0 \times 10^5$ cells/cm$^2$ of growth surface.

Differentiation of Human Pluripotent Stem Cells to Dorsal Neuroectoderm Progenitor Cells and Further to Dorsally-Derived Glial Progenitor Cells and Oligodendrocyte Progenitor Cells The present disclosure provides methods for differentiating human pluripotent stem cells into neuroectoderm with a dorsal spinal cord phenotype and further to glial progenitor cells and oligodendrocyte progenitor cells using a combination of small molecule and protein modulators of BMP signaling and inhibitors of MAPK/ERK kinase. Without being held to any particular theory, the inventors have discovered that human dorsal neuroectoderm progenitor cells obtained in accordance with methods of the present disclosure can be readily and efficiently differentiated into spinal cord OPCs in the absence of activation of SHH signaling. Surprisingly, this early dorsal phenotype, despite not being the region of early OPC generation in vivo, gives rise to glial progenitor cells by day 21 of the differentiation process and to OPCs by day 42 of the differentiation process. The day 42 OPCs produced in accordance with the present disclosure express canonical OPC markers NG2 and PDGFRα and are comparable (in terms of their overall marker expression profile) to OPCs generated using an alternative method that are currently in clinical testing to treat spinal cord injury.

Further, the inventors have discovered that in comparison to differentiation protocols where SHH signaling is activated, the methods of the present disclosure yield a significantly larger number of differentiated cells, providing a scalable process for producing large quantities of dorsal neuroectoderm progenitor cells and their progeny, such as glial progenitor cells or OPCs, for downstream applications.

In an embodiment, a method comprises contacting human pluripotent stem cells with one or more inhibitors of mitogen-activated protein kinase/extracellular signal regulated kinase (MAPK/ERK) combined with one or more inhibitors of bone morphogenic protein (BMP) signaling. In certain embodiments, the MAPK/ERK inhibitor is a small molecule. In other embodiments, the MAPK/ERK inhibitor is a protein, such as a phosphatase that dephosphorylates the MAPK/ERK kinase. In certain embodiments, the inhibitor of BMP signaling is a small molecule. In other embodiments, the inhibitor of BMP signaling is a protein. In some embodiments, the direct target of the inhibitor of BMP signaling is ALK2, also known as Activin A receptor, type I (ACVR1). In certain embodiments, subsequent to MAPK/ERK and BMP signaling inhibition, the cells are cultured in the presence of caudalizing agent retinoic acid, thereby obtaining neuroectoderm-restricted progenitor cells with a dorsal spinal cord phenotype.

In certain embodiments, an inhibitor of MAPK/ERK can be selected from the group consisting of PD0325901, AZD6244, GSK1120212, PD184352 and Cobimetinib, and derivatives thereof. In certain embodiments, an inhibitor of BMP signaling can be selected from the group consisting of Dorsomorphin, DMH-1, K02288, ML347, LDN193189 and Noggin protein.

In an embodiment, a method comprises obtaining undifferentiated human pluripotent stem cells that remain in undifferentiated state; culturing the undifferentiated human pluripotent stem cells adherently in the presence of small molecules PD0325901 and Dorsomorphin and retinoic acid for a first time period; and subsequently culturing the cells adherently in the presence of retinoic acid and in the absence of a SHH signaling activator for a second time period, thereby obtaining dorsal neuroectoderm cells, as depicted in FIG. 1. In an embodiment, the first time period and the second time period can each range from about one to about six days, such as about one day, such as about two days, such as about three days, such as about four days, such as about five days, or such as about six days.

In an embodiment, a method comprises culturing undifferentiated human pluripotent stem cells in the presence of PD0325901 at a concentration that ranges from about 1 μM to about 100 μM, such as about 2 μM, such as about 3 μM, such as about 4 μM, such as about 5 μM, such as about 6 μM, such as about 7 μM, such as about 8 μM, such as about 9 μM, such as about 10 μM, such as about 11 μM, such as about 12 μM, such as about 13 μM, such as about 14 μM, such as about 15 μM, such as about 20 μM, such as about 30 μM, such as about 40 μM, such as about 50 μM, or such as about 60 μM, 70 μM, 80 μM or 90 μM. In another embodiment, a method comprises culturing undifferentiated human pluripotent stem cells in the presence of PD0325901 at a concentration of about 10 μM.

In an embodiment, a method comprises culturing undifferentiated human pluripotent stem cells in the presence of AZD6244 at a concentration that ranges from about 1 μM to about 100 µM, such as about 2 µM, such as about 3 µM, such as about 4 µM, such as about 5 µM, such as about 6 µM, such as about 7 µM, such as about 8 µM, such as about 9 µM, such as about 10 µM, such as about 11 µM, such as about 12 µM, such as about 13 µM, such as about 14 µM, such as about 15 µM, such as about 20 µM, such as about 30 µM, such as about 40 µM, such as about 50 µM, or such as about 60 µM, 70 µM, 80 µM or 90 µM. In another embodiment, a method comprises culturing undifferentiated human pluripotent stem cells in the presence of AZD6244 at a concentration of about 10 µM.

In an embodiment, a method comprises culturing undifferentiated human pluripotent stem cells in the presence of GSK1120212 at a concentration that ranges from about 1 µM to about 100 µM, such as about 2 µM, such as about 3 µM, such as about 4 µM, such as about 5 µM, such as about 6 µM, such as about 7 µM, such as about 8 µM, such as about 9 µM, such as about 10 µM, such as about 11 µM, such as about 12 µM, such as about 13 µM, such as about 14 µM, such as about 15 µM, such as about 20 µM, such as about 30 µM, such as about 40 µM, such as about 50 µM, or such as about 60 µM, 70 µM, 80 µM or 90 µM of PD0325901. In another embodiment, a method comprises culturing undifferentiated human pluripotent stem cells in the presence of GSK1120212 at a concentration of about 10 µM.

In an embodiment, a method comprises culturing undifferentiated human pluripotent stem cells in the presence of PD184352 at a concentration that ranges from about 1 µM to about 100 µM, such as about 2 µM, such as about 3 µM, such as about 4 µM, such as about 5 µM, such as about 6 µM, such as about 7 µM, such as about 8 µM, such as about 9 µM, such as about 10 µM, such as about 11 µM, such as about 12 µM, such as about 13 µM, such as about 14 µM, such as about 15 µM, such as about 20 µM, such as about 30 µM, such as about 40 µM, such as about 50 µM, or such as about 60 µM, 70 µM, 80 µM or 90 µM. In another embodiment, a method comprises culturing undifferentiated human pluripotent stem cells in the presence of PD184352 at a concentration of about 10 µM.

In an embodiment, a method comprises culturing undifferentiated human pluripotent stem cells in the presence of Cobimetinib at a concentration that ranges from about 1 µM to about 100 µM, such as about 2 µM, such as about 3 µM, such as about 4 µM, such as about 5 µM, such as about 6 µM, such as about 7 µM, such as about 8 µM, such as about 9 µM, such as about 10 µM, such as about 11 µM, such as about 12 µM, such as about 13 µM, such as about 14 µM, such as about 15 µM, such as about 20 µM, such as about 30 µM, such as about 40 µM, such as about 50 µM, or such as about 60 µM, 70 µM, 80 µM or 90 µM. In another embodiment, a method comprises culturing undifferentiated human pluripotent stem cells in the presence of Cobimetinib at a concentration of about 10 µM.

In an embodiment, a method comprises culturing undifferentiated human pluripotent stem cells in the presence of Dorsomorphin at a concentration that ranges from about 0.2 µM to about 20 µM, such as about 0.5 µM, such as about 0.8 µM, such as about 1 µM, such as about 1.5 µM, such as about 2 µM, such as about 2.5 µM, such as about 3 µM, such as about 3.5 µM, such as about 4 µM, such as about 4.5 µM, such as about 5 µM, such as about 5.5 µM, such as about 6 µM, such as about 6.5 µM, such as about 7 µM, such as about 7.5 µM, such as about 8 µM, such as about 8.5 µM, such as about 9 µM, such as about 10 µM, such as about 11 µM, such as about 12 µM, such as about 13 µM, such as about 14 µM, such as about 15 µM, such as about 16 µM, such as about 17 µM, such as about 18 µM, or such as about 19 µM. In another embodiment, a method comprises culturing undifferentiated human pluripotent stem cells in the presence of Dorsomorphin at a concentration that ranges from about 0.2 µM to about 1 µM, such as about 0.2 µM to about 0.9 µM, such as about 0.3 µM to about 0.8 µM, such as about 0.4 µM to about 0.7 µM, or such as about 0.5 µM to about 0.6 µM. In yet another embodiment, a method comprises culturing undifferentiated human pluripotent stem cells in the presence of Dorsomorphin at a concentration that ranges from about 1 µM to about 10 µM, such as about 1 µM to about 9 µM, such as about 2 µM to about 8 µM, such as about 3 µM to about 7 µM, or such as about 4 µM to about 6 µM. In an embodiment, a method comprises culturing undifferentiated human pluripotent stem cells in the presence of Dorsomorphin at a concentration that ranges from about 10 µM to about 20 µM, such as about 10 µM to about 19 µM, such as about 12 µM to about 18 µM, such as about 13 µM to about 17 µM, or such as about 14 µM to about 16 µM. In an embodiment, a method comprises culturing undifferentiated human pluripotent stem cells in the presence of Dorsomorphin at a concentration of about 2 µM.

In an embodiment, a method comprises culturing undifferentiated human pluripotent stem cells in the presence of an ALK2 inhibitor at a concentration that ranges from about 1 nM to about 20 µM, such as about 10 nM, about 50 nM, about 100 nM, about 150 nM, about 200 nM, about 500 nM, about 1 µM, about 5 µM, about 10 µM, or about 15 µM.

In an embodiment, a method comprises culturing undifferentiated human pluripotent stem cells in the presence of DMH-1 at a concentration that ranges from about 1 µM to about 10 µM. In an embodiment, a method comprises culturing undifferentiated human pluripotent stem cells in the presence of DMH-1 at about 2 µM.

In an embodiment, a method comprises culturing undifferentiated human pluripotent stem cells in the presence of K02288 at a concentration that ranges from about 1 µM to about 10 µM. In an embodiment, a method comprises culturing undifferentiated human pluripotent stem cells in the presence of K02288 at about 2 µM.

In an embodiment, a method comprises culturing undifferentiated human pluripotent stem cells in the presence of ML347 at a concentration that ranges from about 1 µM to about 10 µM. In an embodiment, a method comprises culturing undifferentiated human pluripotent stem cells in the presence of ML347 at about 2 µM.

In an embodiment, a method comprises culturing undifferentiated human pluripotent stem cells in the presence of LDN193189 at a concentration that ranges from about 1 µM to about 10 µM. In an embodiment, a method comprises culturing undifferentiated human pluripotent stem cells in the presence of LDN193189 at about 2 µM.

Any tissue culture vessels suitable for adherent cell culture may be used for obtaining dorsal neuroectoderm progenitor cells in accordance with the present disclosure. Suitable growth substrates include, for example, recombinant laminin, vitronectin, laminin-511 recombinant fragment E8 or a Matrigel® matrix (e.g., Matrigel®, Matrigel® GFR). In certain embodiments of the present disclosure, the growth substrate is recombinant human laminin-521 (Biolamina, Sweden, distributed by Corning Inc., Corning, N.Y.). In other embodiments, the substrate is a synthetic substrate, such as, for example, Synthemax®-II SC Substrate.

In an embodiment, the dorsal neuroectoderm progenitor cells obtained in accordance with the present disclosure can be harvested and cultured further as aggregates in suspension culture in the presence of bFGF and EGF until the cells have matured into glial progenitor cells. In an embodiment, the further culturing period can range from about five to fifteen days, such as about five days, about six days, about seven days, about eight days, about nine days, about ten days, about eleven days, about twelve days, about thirteen days, about fourteen days, or about fifteen days. In an embodiment, the further culturing period is about seven days.

In an embodiment, adherently cultured dorsal neuroectoderm progenitor cells can be harvested by enzymatic means, such as using TrypLE™ Select (Thermo Fisher Scientific, Waltham, Mass.), Accutase® (Sigma Aldrich, Mo.) or similar trypsinases. Alternatively, adherently cultured dorsal neuroectoderm progenitor cells can be harvested using non-enzymatic means, such as 0.5 mM EDTA in PBS, or such as using ReLeSR™ (Stem Cell Technologies, Vancouver, Canada).

Any cell culture vessels or reactors suitable for suspension culture can be used for the non-adherent culture steps contemplated in the present disclosure. The vessel walls are typically inert or resistant to adherence of the cultured cells. For dynamic suspension, there is also a means for preventing the cells from settling out, such as a stirring mechanism like a magnetically or mechanically driven stir bar or paddle, a shaking mechanism (typically attached to the vessel by the outside), or an inverting mechanism (i.e., a device that rotates the vessel so as to change the direction of gravity upon the cells).

Vessels suitable for suspension culture for process development include the usual range of commercially available spinner, spinner flasks, rocker bag, or shaker flasks. Exemplary bioreactors suitable for commercial production include the VerticalWheel™ Bioreactors (PBS Biotech, Camarillo, Calif.).

Aggregates can also be formed prior to dynamic suspension. For example, the cells can be placed on AggreWell™ plates to generate uniform cell aggregates. After about three days, the cell aggregates can be transferred to dynamic suspension.

In an embodiment, glial progenitor cells obtained in accordance with the present disclosure can be harvested, plated down and cultured adherently for a further time period in the presence of epidermal growth factor (EGF) until the cells have matured into oligodendrocyte progenitor cells. In certain embodiments, the culture medium additionally comprises platelet-derived growth factor AA (PDGF-AA). In an embodiment, the further culturing period can range from about from about ten to thirty days, such as about ten days, about fifteen days, about twenty days, about twenty-five days, or about thirty days. In an embodiment, the further culturing period ranges from about fifteen to twenty-five days, such as about fifteen days, about sixteen days, about seventeen days, about nineteen days, about twenty days, about twenty-one days, about twenty-two days, about twenty-three days, about twenty-four days, or about twenty-five days. In an embodiment, the further culturing period is about twenty-one days.

OPC Compositions

The methods of the present disclosure can be used to obtain compositions comprising oligodendrocyte progenitor cells (OPCs) that are suitable for cellular therapy. The OPCs obtained according to the present disclosure express a high level of the proteoglycan NG2, PDGFRα, and/or GD3 characteristic of OPCs and low levels of non-OPC markers associated with undesirable cell types, such as CD49f, which can be expressed by both neural progenitor cells and epithelial cells and is associated with in vitro cyst formation (Debnath J, Muthuswamy SK, Brugge JS. Morphogenesis and oncogenesis of MCF-10A mammary epithelial acini grown in three-dimensional basement membrane cultures. 2003 Methods. 3:256-68), or CLDN6 and EpCAM, two markers expressed by both pluripotent cells and epithelial cells (Lin D, Guo Y, Li Y, Ruan Y, Zhang M, Jin X, Yang M, Lu Y, Song P, Zhao S, Dong B, Xie Y, Dang Q, Quan C. Bioinformatic analysis reveals potential properties of human Claudin-6 regulation and functions. *Oncol Rep.* 2017 August; 38(2):875-885; Huang L, Yang Y, Yang F, Liu S, Zhu Z, Lei Z, Guo J. Functions of EpCAM in physiological processes and diseases (Review). *Int J Mol Med.* 2018 October; 42(4):1771-1785).

In certain embodiments, the OPCs generated in accordance with the present disclosure are the in vitro differentiated progeny of human pluripotent stem cells. In certain embodiments, the OPCs obtained in accordance of the present disclosure are the in vitro differentiated progeny of human embryonic stem cells. In other embodiments, the OPCs obtained in accordance of the present disclosure are the in vitro differentiated progeny of induced pluripotent stem (iPS) cells.

One or more characteristics of the OPC population obtained can be determined by quantifying various cell markers using flow cytometry, for example, to determine what percentage of the cell population is positive for a particular marker or set of markers or to identify undesirable cell types present in the OPC population.

An OPC population obtained according to the present disclosure can comprise from about 30% to about 100% NG2 positive cells, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 98%, such as at least about 99%, such as at least about 99.5%, such as at least about 99.8%, or such as at least about 99.9% NG2 positive cells. In certain embodiments, an OPC population obtained according to the present disclosure can comprise from about 45% to about 75% NG2 positive cells, such as about 45% to about 50%, such as about 50% to about 55%, such as about 55% to about 60%, such as about 60% to about 65%, such as about 65% to about 70%, such as about 70% to about 75%, such as about 50% to about 70%, such as about 55% to about 65%, or such as about 58% to about 63% NG2 positive cells. In other embodiments, an OPC population obtained according to the present disclosure can comprise from about 60% to about 90% NG2 positive cells, such as about 60% to about 65%, such as about 65% to about 70% positive cells.

An OPC population obtained according to the present disclosure can comprise from about 30% to about 100% PDGFRα positive cells, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 98%, such as at least about 99%, such as at least about 99.5%, such as at least about 99.8%, or such as at least about 99.9% PDGFRα positive cells. In certain embodiments, an OPC population obtained according to the present disclosure can comprise from about 45% to about 75% PDGFRα positive cells, such as about 45% to about 50%, such as about 50% to about 55%, such as about 55% to about 60%, such as about 60% to about 65%, such as about 65% to about 70%, such as about 70% to about 75%, such as about 50% to about 70%, such as about 55% to about 65%, or such as about 58% to about 63% PDGFRα positive cells. In other embodiments, an OPC population obtained according to the present disclosure can comprise from about 60% to about 90% PDGFRα positive cells, such as about 60% to about 65%, such as about 65% to about 70% positive cells.

An OPC population obtained according to the present disclosure can comprise from about 30% to about 100% GD3 positive cells, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 98%, such as at least about 99%, such as at least about 99.5%, such as at least about 99.8%, or such as at least about 99.9% GD3 positive cells. In certain embodiments, an OPC population obtained according to the present disclosure can comprise from about 45% to about 75% GD3 positive cells, such as about 45% to about 50%, such as about 50% to about 55%, such as about 55% to about 60%, such as about 60% to about 65%, such as about 65% to about 70%, such as about 70% to about 75%, such as about 50% to about 70%, such as about 55% to about 65%, or such as about 58% to about 63% GD3 positive cells. In other embodiments, an OPC population obtained according to the present disclosure can comprise from about 60% to about 90% GD3 positive cells, such as about 60% to about 65%, such as about 65% to about 70% positive cells.

In an embodiment, an OPC population obtained according to the present disclosure can be capable of forming less than or equal to four epithelial cysts per 100,000 cells in a cyst assay as described in Example 8 of the present disclosure. In another embodiment, an OPC population obtained according to the present disclosure can be capable of forming less than or equal to three epithelial cysts per 100,000 cells in a cyst assay. In another embodiment, OPC population obtained according to the present disclosure can be capable of forming less than or equal to two epithelial cysts per 100,000 cells in a cyst assay. In yet another embodiment, an OPC population obtained according to the present disclosure can be capable of forming less than or equal to one epithelial cysts per 100,000 cells in a cyst assay as described in Example 8 of the present disclosure.

Undesirable Cell Types

OPC populations obtained according to the present disclosure contain low levels of undesired ell types, as measured, for example, by quantification of markers associated with undesirable cell types by flow cytometry. In a non-limiting example, the Day 42 OPCs obtained according to the present disclosure may contain low levels of cells expressing the epithelial cell associated markers EpCAM, CD49f, and CLDN6.

Markers associated with undesirable cell types can comprise less than about 20% undesirable cell types, such as less than about 19%, such as less than about 18%, such as less than about 17%, such as less than about 16%, such as less than about 15%, such as less than about 14%, such as less than about 13%, such as less than about 12%, such as less than about 11%, such as less than about 10%, such as less than about 9%, such as less than about 8%, such as less than about 7%, such as less than about 6%, such as less than about 5%, such as less than about 4%, such as less than about 3%, such as less than about 2%, such as less than about 1%, such as less than about 0.5%, such as less than about 0.1%, such as less than about 0.05%, or such as less than about 0.01% undesirable cell types. In another embodiment, a cell population can comprise from about 15% to about 20% undesirable cell types, such as about 19% to about 20%, such as about 18% to about 20%, such as about 17% to about 20%, such as about 16% to about 20%, such as about 15% to about 19%, or such as about 16% to about 18% undesirable cell types. In yet another embodiment, a cell population can comprise from about 10% to about 15% undesirable cell types, such as about 14% to about 15%, such as about 13% to about 15%, such as about 12% to about 15%, such as about 11% to about 15%, or such as about 12% to about 14% undesirable cell types. In an embodiment, a cell population can comprise from about 1% to about 10% undesirable cell types, such as about 2% to about 10%, such as about 1% to about 9%, such as about 2% to about 8%, such as about 3% to about 7%, or such as about 4% to about 6% undesirable cell types. In an embodiment, a cell population can comprise from about 0.1% to about 1% undesirable cell types, such as about 0.2% to about 1%, such as about 0.1% to about 0.9%, such as about 0.2% to about 0.8%, such as about 0.3% to about 0.7%, or such as about 0.4% to about 0.6% undesirable cell types. In an embodiment, a cell population can comprise from about 0.01% to about 0.1% undesirable cell types, such as about 0.02% to about 0.1%, such as about 0.01% to about 0.09%, such as about 0.02% to about 0.08%, such as about 0.03% to about 0.07%, or such as about 0.04% to about 0.06% undesirable cell types. In an embodiment, low levels of undesirable cell types can denote the presence of less than about 15% undesirable cell types.

In an embodiment, an undesirable cell type can comprise cells expressing one or more markers selected from CD49f, CLDN6, or EpCAM.

Cryopreservation

Following harvesting, the expanded population of OPCs can be formulated at a specific therapeutic dose (e.g., number of cells) and cryopreserved for shipping to the clinic. The ready to administer (RTA) OPC therapy composition can then be administered directly after thawing without further processing. Examples of media suitable for cryopreservation include but are not limited to 90% Human Serum/10% DMSO, Media 3 10% (CS10), Media 2 5% (CS5) and Media 1 2% (CS2), Stem Cell Banker, PRIME XV® FREEZIS, HYPOTHERMASOL®, CSB, Trehalose, etc.

In some embodiments, the percent viability of post-filtered cells stored in a cryopreservation medium for between about 0 to about 8 hours is at least about 75%, 80%, 85%, 90%, 91%, 92%, 93%, 94%, 95%, 96%, 97%, 98%, 99%, or 100%. In other embodiments, the percent recovery of post-filtered cells stored in a cryopreservation medium for between about 0 to about 8 hours is at least about 75%, 80%, 85%, 90%, 91%, 92%, 93%, 94%, 95%, 96%, 97%, 98%, 99%, or 100%.

In further embodiments, the percent viability of post-filtered cells stored in a neutralization medium for between about 0 to about 8 hours followed by storage in cryopreservation medium for between about 0 to about 8 hours is at least about 75%, 80%, 85%, 90%, 91%, 92%, 93%, 94%, 95%, 96%, 97%, 98%, 99%, or 100%. In other embodiments, the percent recovery of post-filtered cells stored in a neutralization medium for between about 0 to about 8 hours followed by storage in cryopreservation medium for between about 0 to about 8 hours is at least about 70%, 75%, 80%, 85%, 90%, 91%, 92%, 93%, 94%, 95%, 96%, 97%, 98%, 99%, or 100%.

In yet other embodiments, the percent viability of post-filtered cells stored in a neutralization medium for between about 0 to about 8 hours followed by storage in cryopreservation medium for between about 0 to about 8 hours, post-thawing of the cryopreserved composition, is at least about 75%, 80%, 85%, 90%, 91%, 92%, 93%, 94%, 95%, 96%, 97%, 98%, 99%, or 100%. In still other embodiments, the percent recovery of post-filtered cells stored in a neutralization medium for between about 0 to about 8 hours followed by storage in cryopreservation medium for between about 0 to about 8 hours, post-thawing of the cryopreserved composition, is at least about, 70%, 75%, 80%, 85%, 90%, 91%, 92%, 93%, 94%, 95%, 96%, 97%, 98%, 99%, or 100%.

In some embodiments, post-filtered OPCs stored in a neutralization medium for between about 0 to about 8 hours followed by storage in cryopreservation medium for between about 0 to about 8 hours, post-thawing of the cryopreserved composition are capable of secreting Decorin. In other embodiments, post-filtered OPCs stored in a neutralization medium for between about 0 to about 8 hours followed by storage in cryopreservation medium for between about 0 to about 8 hours, post-thawing of the cryopreserved composition are capable of being expanded.

In some embodiments, the percent viability of post-filtered OPCs stored in a neutralization medium for between about 0 to about 8 hours at room temperature is at least about, 70%, 75%, 80%, 85%, 90%, 91%, 92%, 93%, 94%, 95%, 96%, 97%, 98%, 99%, or 100%. In some embodiments, the percent viability of post-filtered OPCs stored in a cryopreservation medium for between about 0 to about 8 hours at room temperature is at least about, 70%, 75%, 80%, 85%, 90%, 91%, 92%, 93%, 94%, 95%, 96%, 97%, 98%, 99%, or 100%. In further embodiments, the percent viability of post-filtered cells stored in a neutralization solution at room temperature for between about 0 to about 8 hours followed by storage in cryopreservation medium for between about 0 to about 8 hours at room temperature is at least about 75%, 80%, 85%, 90%, 91%, 92%, 93%, 94%, 95%, 96%, 97%, 98%, 99%, or 100%. In still further embodiments, the percent recovery of post-filtered cells stored in a neutralization solution at room temperature for between about 0 to about 8 hours followed by storage in cryopreservation medium for between about 0 to about 8 hours at room temperature is at least about 75%, 80%, 85%, 90%, 91%, 92%, 93%, 94%, 95%, 96%, 97%, 98%, 99%, 100%, 105%, 110%, 115%, 120%, 125%, 130%, 140%, 150%.

OPCs formulated in cryopreservation media appropriate for post thaw ready to administer (RTA) applications may comprise OPCs suspended in adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water. An example of this cryopreservation media is available commercially under the tradename, CRYOSTOR® and is manufactured by BioLife Solutions, Inc.

DMSO can be used as a cryoprotective agent to prevent the formation of ice crystals, which can kill cells during the cryopreservation process. In some embodiments, the cryopreservable OPC therapy composition comprises between about 0.1% and about 2% DMSO (v/v). In some embodiments, the RTA OPC therapy composition comprises between about 1% and about 20% DMSO. In some embodiments, the RTA OPC therapy composition comprises about 10% DMSO. In some embodiments, the RTA OPC cell therapy composition comprises about 5% DMSO.

In some embodiments, OPC therapies formulated in cryopreservation media appropriate for post thaw ready to administer (RTA) applications may comprise OPCs suspended in cryopreservation media that does not contain DMSO. For example, RTA OPC therapeutic cell compositions may comprise OPCs suspended in Trolox, Na+, K+, Ca2+, Mg2+, c1−, H2P04−, HEPES, lactobionate, sucrose, mannitol, glucose, dextran-40, adenosine, glutathione without DMSO (dimethyl sulfoxide, $(CH_3)_2SO$) or any other dipolar aprotic solvents. An example of this cryopreservation media is available commercially under the tradename, HYPOTHERMOSOL® or HYPOTHERMOSOL®-FRS and is also manufactured by BioLife Solutions, Inc. In other embodiments, OPC compositions formulated in cryopreservation media appropriate for post thaw ready to administer applications may comprise OPCs suspended in Trehalose.

The RTA OPC therapy composition may optionally comprise additional factors that support OPC engraftment, integration, survival, potency, etc. In some embodiments, the RTA OPC therapy composition comprises activators of function of the OPC preparations described herein.

In some embodiments, the RTA OPC therapy composition may be formulated in a medium comprising components that decrease the molecular cell stress during freezing and thawing processes by scavenging of free radicals, pH buffering, oncotic/osmotic support and maintenance of the ionic concentration balance.

In some embodiments, OPC therapies formulated in cryopreservation media appropriate for post thaw ready to administer applications may comprise one or more immunosuppressive compounds. In certain embodiments, OPC therapies formulated in cryopreservation media appropriate for post thaw ready to administer applications may comprise one or more immunosuppressive compounds that are formulated for slow release of the one or more immunosuppressive compounds. Immunosuppressive compounds for use with the formulations described herein may belong to the following classes of immunosuppressive drugs: Glucocorticoids, Cytostatics (e.g. alkylating agent or antimetabolite), antibodies (polyclonal or monoclonal), drugs acting on immunophilins (e.g. cyclosporin, Tacrolimus or Sirolimus). Additional drugs include interferons, opioids, TNF binding proteins, mycophenolate and small biological agents. Examples of immunosuppressive drugs include: mesenchymal stem cells, anti-lymphocyte globulin (ALG) polyclonal antibody, anti-thymocyte globulin (ATG) polyclonal antibody, azathioprine, BAS 1L1 X 1MAB® (anti-I L-2Ra receptor antibody), cyclosporin (cyclosporin A), DACLIZUMAB® (anti-I L-2Ra receptor antibody), everolimus, mycophenolic acid, RITUX 1MAB® (anti-CD20 antibody), sirolimus, tacrolimus, Tacrolimus and or Mycophenolate mofetil.

Formulation

OPC compositions in accordance with the present disclosure can further comprise a pharmaceutically-acceptable carrier. In an embodiment, a pharmaceutically-acceptable carrier can comprise dimethyl sulfoxide (DMSO). In an embodiment, a pharmaceutically-acceptable carrier does not comprise dimethyl sulfoxide. As mentioned above, a composition can be further adapted for cryopreservation at or below −80° C. to −195° C.

OPC compositions in accordance with the present disclosure can be formulated for administration via a direct injection to the spinal cord of a subject. In an embodiment, an OPC composition in accordance with the present disclosure can be formulated for intracerebral, intraventricular, intrathecal, intranasal, or intracisternal administration to a subject. In an embodiment, an OPC composition in accordance with the present disclosure can be formulated for administration via an injection directly into or immediately adjacent to an infarct cavity in the brain of a subject. In an embodiment, a composition in accordance with the present disclosure can be formulated for administration through implantation. In an embodiment, a composition in accordance with the present disclosure can be formulated as a solution.

An OPC composition in accordance with the present disclosure can comprise from about $1 \times 10^6$ to about $5 \times 10^8$ cells per milliliter, such as about $1 \times 10^6$ cells per milliliter, such as about $2 \times 10^6$ cells per milliliter, such as about $3 \times 10^6$ cells per milliliter, such as about $4 \times 10^6$ cells per milliliter, such as about $5 \times 10^6$ cells per milliliter, such as about $6 \times 10^6$ cells per milliliter, such as about $7 \times 10^6$ cells per milliliter, such as about $8 \times 10^6$ cells per milliliter, such as about $9 \times 10^6$ cells per milliliter, such as about $1 \times 10^7$ cells per milliliter, such as about $2 \times 10^7$ cells per milliliter, such as about $3 \times 10^7$ cells per milliliter, such as about $4 \times 10^7$ cells per milliliter, such as about $5 \times 10^7$ cells per milliliter, such as about $6 \times 10^7$ cells per milliliter, such as about $7 \times 10^7$ cells per milliliter, such as about $8 \times 10^7$ cells per milliliter, such as about $9 \times 10^7$ cells per milliliter, such as about $1 \times 10^8$ cells per milliliter, such as about $2 \times 10^8$ cells per milliliter, such as about $3 \times 10^8$ cells per milliliter, such as about $4 \times 10^8$ cells per milliliter, or such as about $5 \times 10^8$ cells per milliliter. In another embodiment, a composition in accordance with the present disclosure can comprise from about $1 \times 10^8$ to about $5 \times 10^8$ cells per milliliter, such as about $1 \times 10^8$ to about $4 \times 10^8$ cells per milliliter, such as about $2 \times 10^8$ to about $5 \times 10^8$ cells per milliliter, such as about $1 \times 10^8$ to about $3 \times 10^8$ cells per milliliter, such as about $2 \times 10^8$ to about $4 \times 10^8$ cells per milliliter, or such as about $3 \times 10^8$ to about $5 \times 10^8$ cells per milliliter. In yet another embodiment, a composition in accordance with the present disclosure can comprise from about $1 \times 10^7$ to about $1 \times 10^8$ cells per milliliter, such as about $2 \times 10^7$ to about $9 \times 10^7$ cells per milliliter, such as about $3 \times 10^7$ to about $8 \times 10^7$ cells per milliliter, such as about $4 \times 10^7$ to about $7 \times 10^7$ cells per milliliter, or such as about $5 \times 10^7$ to about $6 \times 10^7$ cells per milliliter. In an embodiment, a composition in accordance with the present disclosure can comprise from about $1 \times 10^6$ to about $1 \times 10^7$ cells per milliliter, such as about $2 \times 10^6$ to about $9 \times 10^6$ cells per milliliter, such as about $3 \times 10^6$ to about $8 \times 10^6$ cells per milliliter, such as about $4 \times 10^6$ to about $7 \times 10^6$ cells per milliliter, or such as about $5 \times 10^6$ to about $6 \times 10^6$ cells per milliliter. In yet another embodiment, a composition in accordance with the present disclosure can comprise at least about $1 \times 10^6$ cells per milliliter, such as at least about $2 \times 10^6$ cells per milliliter, such as at least about $3 \times 10^6$ cells per milliliter, such as at least about $4 \times 10^6$ cells per milliliter, such as at least about $5 \times 10^6$ cells per milliliter, such as at least about $6 \times 10^6$ cells per milliliter, such as at least about $7 \times 10^6$ cells per milliliter, such as at least about $8 \times 10^6$ cells per milliliter, such as at least about $9 \times 10^6$ cells per milliliter, such as at least about $1 \times 10^7$ cells per milliliter, such as at least about $2 \times 10^7$ cells per milliliter, such as at least about $3 \times 10^7$ cells per milliliter, such as at least about $4 \times 10^7$ cells per milliliter, or such as at least about $5 \times 10^7$ cells per milliliter. In an embodiment, a composition in accordance with the present disclosure can comprise up to about $1 \times 10^8$ cells or more, such as up to about $2 \times 10^8$ cells per milliliter or more, such as up to about $3 \times 10^8$ cells per milliliter or more, such as up to about $4 \times 10^8$ cells per milliliter or more, such as up to about $5 \times 10^8$ cells per milliliter or more, or such as up to about $6 \times 10^8$ cells per milliliter.

In an embodiment, an OPC composition in accordance with the present disclosure can comprise from about $4 \times 10^7$ to about $2 \times 10^8$ cells per milliliter.

In yet another embodiment, an OPC composition in accordance with the present disclosure can have a volume ranging from about 10 microliters to about 5 milliliters, such as about 20 microliters, such as about 30 microliters, such as about 40 microliters, such as about 50 microliters, such as about 60 microliters, such as about 70 microliters, such as about 80 microliters, such as about 90 microliters, such as about 100 microliters, such as about 200 microliters, such as about 300 microliters, such as about 400 microliters, such as about 500 microliters, such as about 600 microliters, such as about 700 microliters, such as about 800 microliters, such as about 900 microliters, such as about 1 milliliter, such as about 1.5 milliliters, such as about 2 milliliters, such as about 2.5 milliliters, such as about 3 milliliters, such as about 3.5 milliliters, such as about 4 milliliters, or such as about 4.5 milliliters. In an embodiment, a composition in accordance with the present disclosure can have a volume ranging from about 10 microliters to about 100 microliters, such as about 20 microliters to about 90 microliters, such as about 30 microliters to about 80 microliters, such as about 40 microliters to about 70 microliters, or such as about 50 microliters to about 60 microliters. In another embodiment, a composition in accordance with the present disclosure can have a volume ranging from about 100 microliters to about 1 milliliter, such as about 200 microliters to about 900 microliters, such as about 300 microliters to about 800 microliters, such as about 400 microliters to about 700 microliters, or such as about 500 microliters to about 600 microliters. In yet another embodiment, a composition in accordance with the present disclosure can have a volume ranging from about 1 milliliter to about 5 milliliters, such as about 2 milliliter to about 5 milliliters, such as about 1 milliliter to about 4 milliliters, such as about 1 milliliter to about 3 milliliters, such as about 2 milliliter to about 4 milliliters, or such as about 3 milliliter to about 5 milliliters. In an embodiment, an OPC composition in accordance with the present disclosure can have a volume of about 20 microliters to about 500 microliters. In another embodiment, an OPC composition in accordance with the present disclosure can have a volume of about 50 microliters to about 100 microliters. In yet another embodiment, an OPC composition in accordance with the present disclosure can have a volume of about 50 microliters to about 200 microliters. In another embodiment, an OPC composition in accordance with the present disclosure can have a volume of about 20 microliters to about 400 microliters. In an embodiment, an OPC composition in accordance with the present disclosure can be in a container configured for cryopreservation or for administration to a subject in need thereof. In an embodiment, a container can be a prefilled syringe.

Methods of Use

An OPC composition obtained in accordance with the present disclosure can be used in cellular therapy to improve one or more neurological functions in a subject in need of treatment. In an embodiment, an OPC cell population in accordance with the present disclosure can be injected or implanted into a subject in need thereof. In an embodiment, a cell population in accordance with the present disclosure can be implanted into a subject in need thereof for treating spinal cord injury, stroke, or multiple sclerosis.

In an embodiment, a cell population in accordance with the present disclosure can be capable of inducing myelination of denuded axons at an implantation site in a subject. In an embodiment, a cell population generated in accordance with a method of the present disclosure can exhibit improved capacity for engraftment and migration. In an embodiment, a cell population generated in accordance with a method of the present disclosure can be capable of improving post-injury repair or regeneration of neural tissue in a subject.

A cell population in accordance with the present disclosure can be capable of improving a sensory function in a subject in need of therapy following implantation of the population into the subject. Improvements in a sensory function can be evaluated using the International Standards for Neurological Classification of Spinal Cord Injury (ISNCSCI) Exam, such as determining sensory levels for right and left sides for pin prick and light touch sensations. A cell population in accordance with the present disclosure can be capable of improving a motor function in a subject in need of therapy following implantation of the population into the subject. An improved motor function can be evaluated using the ISNCSCI Exam, such as determining motor levels for right and left sides for total paralysis, palpable or visible contraction, active movement, full range of motion against gravity, and sufficient resistance.

A cell population in accordance with the present disclosure can be capable of reducing a volume of an injury-induced central nervous system parenchymal cavitation in 12 months or less. In an embodiment, a cell population in accordance with the present disclosure can be capable of reducing a volume of an injury-induced central nervous system parenchymal cavitation in a subject in 6 months or less, 5 months or less, 4 months or less, 3 months or less, 2 months or less, or less than 1 month.

Having now generally described the invention, the same will be more readily understood through reference to the following examples that are provided by way of illustration, and are not intended to be limiting of the present disclosure, unless specified.

EXAMPLES

Example 1—Culture and Expansion of Undifferentiated Human Embryonic Stem Cells

Undifferentiated human embryonic stem cells (uhESC) from a working cell bank (WCB) generated from the H1 line (WA01; Thomson J A, Itskovitz-Eldor J, Shapiro S S, Waknitz M A, Swiergiel J J, Marshall V S, Jones J M. Embryonic stem cell lines derived from human blastocysts. *Science.* 1998 Nov. 6; 282(5391):1145-7) were cultured on recombinant human Laminin-521 (rhLn-521, Corning #354224) coated, tissue culture treated polystyrene T-75 culture flasks (Corning #431082) in complete mTeSR™-1 medium (Stem Cell Technologies #85850). The medium was completely exchanged daily until the cells reached approximately 80-90% confluency, and uhESCs were then passaged using ReLeSR™ reagent (Stem Cell Technologies #05872). ReLeSR™-lifted uhESC cells were seeded in new rhLn-521 coated 225 cm² flasks, and daily medium exchange was resumed two days post-seeding. Cultured uhESCs from the WCB were expanded in this manner for between two to five passages, depending on the experiment, prior to differentiation into neuroectoderm progenitor cells as described in Example 2.

Example 2—Method of Differentiating Human Embryonic Stem Cells to Neuroectoderm Progenitors with Dorsal Spinal Cord Progenitor Phenotype Expanded uhESC were seeded on rhLn-521-coated vessels, and cultured until reaching 40-70% confluency at which point differentiation was initiated.

Days 0-3:

Differentiation was initiated by complete removal of mTeSR™-1 medium, and addition of Glial Progenitor Medium (GPM; consisting of DMEM/F12 (Gibco Catalog No. 10565-018) supplemented with 2% B27 supplement (Gibco Catalog No. 17504-044), and 0.04 µg/mL tri-iodothyronine (Sigma-Aldrich Catalog No. T5516-1MG)) supplemented with 10 µM of MAPK/ERK inhibitor, PD0325901 (PD; Sigma-Aldrich Catalog No. PZ0162), 2 µM of BMP signaling inhibitor, Dorsomorphin (Dorso; Sigma-Aldrich Catalog No. P5499), and 1 µM of Retinoic Acid (RA; Sigma-Aldrich Catalog No. R2625). This medium was replenished daily.

Days 4-6:

On Day 4, culture medium was switched to GPM supplemented with 1 µM RA and 150 µM Ascorbic Acid (Sigma-Aldrich Catalog No. A4544) and replenished daily.

Day 7:

On Day 7, the cells were harvested for expansion and further differentiation into glial progenitors as described in Example 3. A subset of cells were collected for analysis by quantitative PCR (qPCR; as described in Example 6), flow cytometry (as described in Example 5), and when available, separate well plates set aside for analysis were prepared for immunocytochemistry (ICC) (as described in Example 5). At Day 7, these cells exhibited marker expression consistent with dorsal spinal cord progenitors (TABLE 2, FIG. 3).

Example 3—Method of Differentiating Human Embryonic Stem Cells to Glial Lineage Cells Days 7-13:

Differentiation of uhESCs to neuroectoderm progenitors, specifically of a dorsal phenotype, was performed as described in Example 2. On Day 7, the cells were lifted using TrypLE™ Select (Thermo Fisher, cat #A12859-01), counted, and seeded onto rhLn-521-coated vessels at a seeding density of $2.7 \times 10^4$ cells/cm² in GPM supplemented with 20 ng/mL human basic fibroblast growth factor (hbFGF, Thermo Fisher, cat #PHG0263), 10 ng/mL epidermal growth factor (EGF, Thermo Fisher, cat #PHG0311), and 10 µM Rho Kinase Inhibitor (RI, Tocris Catalog No. 1254). Culture medium was replenished daily by aspirating spent medium and replacing it with fresh GPM+hbFGF+EGF.

Days 14-21:

At Day 14, cells were lifted using TrypLE™ Select, counted, resuspended in GPM+hbFGF+EGF+RI, and reseeded in dynamic suspension cultures at a density of $1.83 \times 10^6$ viable cells/mL into either PBS-0.1L or PBS-0.5L Mini Bioreactor Systems (PBS Biotech). Subsets of cells at Day 14 were collected for analysis by flow cytometry (Example 5), ICC (Example 5), and qPCR (Example 6). PBS0.1L and PBS0.5L Mini Bioreactors were set to rotate at 35 RPM and 28 RPM, respectively. Culture medium was replenished daily by allowing the aggregates to settle, removing 70-80% of spent medium, and replacing with an equal volume of GPM+bhFGF+EGF. On Day 15, the rotation velocity was increased to 45 RPM and 32 RPM for the PBS0.1L and PBS0.5L Mini Bioreactors, respectively.

At Day 21, subsets of the aggregates were collected for ICC (Example 5) and qPCR (Example 6). By Day 21, the differentiated cells expressed markers consistent with glial-restricted cells (TABLE 2, FIG. 4).

Example 4—Method of Differentiating Human Embryonic Stem Cells to Oligodendrocyte Progenitor Cells Days 21-42:

The glial-restricted progenitor cells obtained in Example 3 were further differentiated into oligodendrocyte progenitor cells (OPCs). The differentiation protocol for Days 0-20 was performed as described in Examples 2 and 3. On Day 21, aggregates were transferred from dynamic suspension to rhLn-521-coated culture vessels. For example, starting with 1×PBS-0.1L Mini Bioreactor with 60 mL of total volume, the 60 mL of culture was split onto 2×T75 flasks, each with 30 mL of volume. Subsequently, cells were fed every other day with GPM supplemented with 20 ng/mL EGF and 10 ng/mL of platelet-derived growth factor AA (PDGFAA; PeproTech, cat #AF-100-13A). Every seven days, (i.e., Day 28 and Day 35), cells were lifted with TrypLE™ Select, counted, and reseeded onto fresh rhLn-521-coated culture vessels at a seeding density of $4 \times 10^4$ viable cells/cm$^2$.

The differentiated cells were harvested on Day 42. Cells were detached from vessels using TrypLE™ Select, counted, and re-formulated in CryoStor10 (BioLife Solutions, cat #210102) prior to cryopreservation. Subsets of cells were collected for analysis by flow cytometry (Example 5), ICC (Example 5), and qPCR (Example 6). By Day 42, the differentiated cells expressed markers characteristic with OPCs as measured by the three analytical methods (TABLE 1, TABLE 2, FIG. 5).

Example 5—Characterization of Differentiated Cell Populations by Immunocytochemistry and Flow Cytometry Flow cytometry and immunocytochemistry (ICC) can be used to detect and characterize different aspects of protein marker expression in a cell population. While flow cytometry can be used to quantify the percentage of individual cells within the population that exhibit a given protein marker profile, ICC provides additional information about the subcellular localization of each protein marker and can be applied to single cells or cellular aggregates. By using either or both of these protein profiling approaches, we tracked the differentiation of human embryonic stem cells to neuroectoderm progenitor cells, glial progenitor cells, and oligodendrocyte progenitor cells according to the methods of the present disclosure.

For human embryonic stem cells differentiated into neuroectoderm progenitor cells and glial progenitor cells, protein marker expression in the differentiated Day 7 and Day 21 cells was characterized by ICC. Adherent cells and cellular aggregates were fixed in 4% paraformaldehyde (PFA) for 30 minutes at room temperature (RT). Fixed cells and aggregates were washed with phosphate buffered saline (PBS), and fixed aggregates were then sequentially placed in increasing concentrations of sucrose solution (10%, 20%, and 30% weight/volume) for 30 minutes at RT, 30 minutes at RT, and overnight at 4° C., respectively. Following sucrose replacement, aggregates were embedded in Tissue-Tek Optimal Cutting Temperature (OCT) solution (Sakura Finetek USA #4583) and frozen at −80° C. OCT-embedded aggregates were warmed to −20° C., cut into 30 μm sections using a cryostat (model CM3050 S, Leica Biosystems, Buffalo Grove, Ill., USA), and mounted onto poly-L-lysine (Sigma-Aldrich #P4707) coated glass slides. To perform immunocytochemical staining, fixed adherent cells and slide-mounted aggregate sections were permeabilized and blocked in blocking solution consisting of 0.1% Triton™ X-100/2% normal goat serum/1% bovine serum albumin in PBS for 2 hours at room temperature (RT). Following permeabilization and blocking, adherent cells and aggregate sections were incubated overnight at 4° C. in blocking solution without Triton™ X-100 and containing primary antibodies specific to protein markers of interest, including PAX6 (BD Pharmingen #561462 or BioLegend #901301) to detect neuroectoderm progenitors, and AP2 (Developmental Studies Hybridoma Bank—DSHB #3B5), PAX3 (DSHB #Pax3), and PAX7 (DSHB #Pax7) to detect dorsal spinal cord progenitor cells. Adherent cells and aggregate sections were then washed three times with PBS followed by incubation with secondary antibodies specific to the chosen primary antibodies and 4′,6-diamidino-2-phenylindole (DAPI) counter-stain in blocking solution without Triton™ X-100 for 1 hour at RT protected from light. Adherent cells and aggregate sections were washed three times with PBS and imaged using an IN Cell Analyzer 2000 (GE Healthcare, Pittsburgh, Pa., USA).

Figure 3:
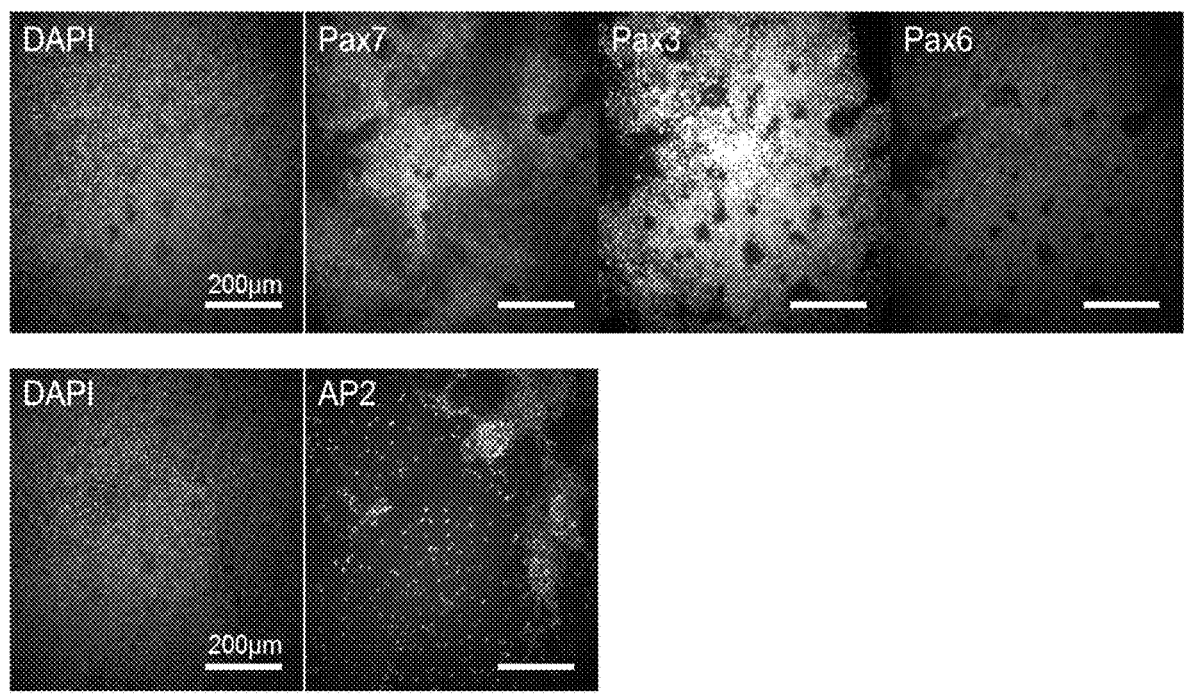
FIG. 3 shows representative photomicrographs of dorsal neuroectoderm progenitor cells generated in accordance with the present disclosure and stained by immunocytochemistry. Dorsal neuroectoderm progenitor cells were stained for DAPI, PAX7, PAX3 and PAX6 (top panels, left to right), and DAPI and AP2 (bottom panels, left to right). Stained cells were imaged on an IN Cell Analyzer 2000. Scale bar represents 200 μm and applies to all images in the figure.

FIG. 3 shows representative ICC data for the Day 7 neuroectoderm progenitor cells exhibiting a dorsal spinal cord progenitor phenotype. After 7 days of differentiation, the adherent cell population from two representative experiments expressed PAX6, a protein marker characteristic of neuroectoderm progenitor cells (Lippmann E S, Williams C E, Ruhl D A, Estevez-Silva M C, Chapman E R, Coon J J, Ashton R S. Deterministic HOX patterning in human pluripotent stem cell-derived neuroectoderm. Stem Cell Reports. 2015 Apr. 14; 4(4):632-44; Kim D S, Lee D R, Kim H S, Yoo J E, Jung S J, Lim B Y, Jang J, Kang H C, You S, Hwang D Y, Leem J W, Nam T S, Cho S R, Kim D W. Highly pure and expandable PSA-NCAM-positive neural precursors from human ESC and iPSC-derived neural rosettes. *PLoS One*. 2012; 7(7):e39715) and also expressed the dorsal spinal cord progenitor markers, AP2, PAX3, and PAX7 (Le Dréau G, Marti E. Dorsal-ventral patterning of the neural tube: a tale of three signals. Dev Neurobiol. 2012 December; 72(12):1471-81; Marklund U, Alekseenko Z, Andersson E, Falci S, Westgren M, Perlmann T, Graham A, Sundström E, Ericson J. Detailed expression analysis of regulatory genes in the early developing human neural tube. Stem Cells Dev. 2014 Jan. 1; 23(1):5-15).

Figure 4:
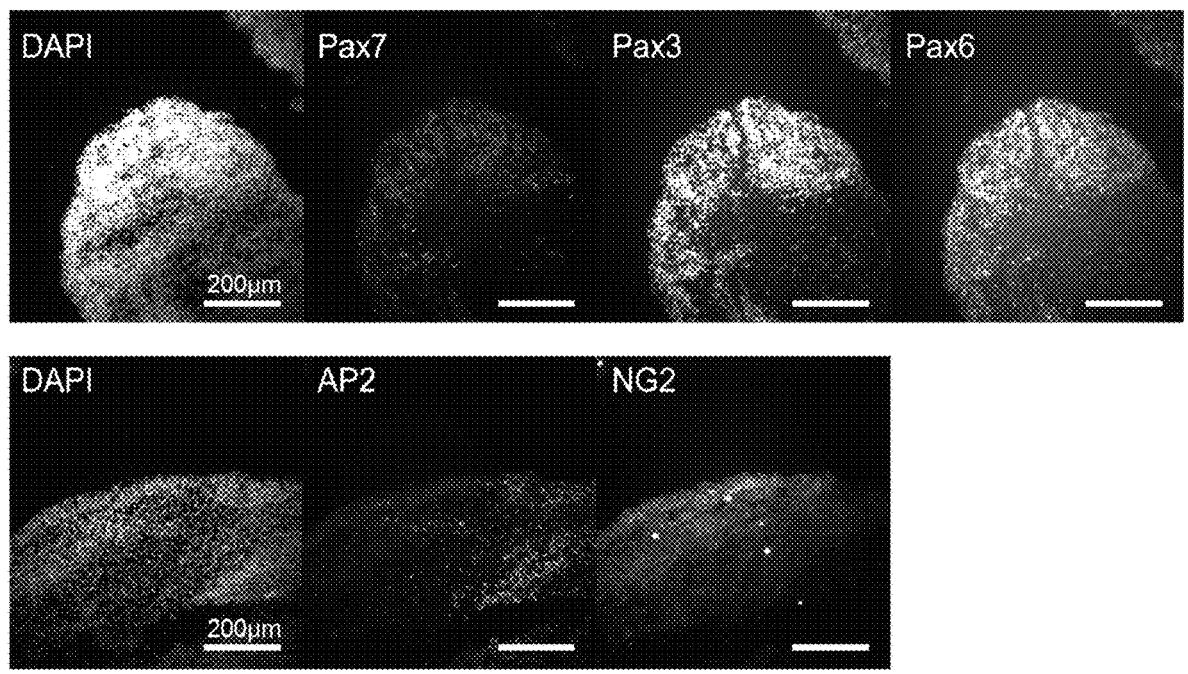
FIG. 4 shows representative photomicrographs of aggregates of glial progenitor cells generated in accordance with the present disclosure and stained by immunocytochemistry. Glial progenitor cells were stained for DAPI, PAX7, PAX3, and PAX6 (top panels, left to right) and DAPI, AP2 and NG2 (bottom panels, left to right). Stained cells were imaged on an IN Cell Analyzer 2000. Scale bar represents 200 μm and applies to all images in the figure.

FIG. 4 shows representative ICC data for the Day 21 glial progenitor cells. Aggregates were sectioned and stained for dorsal progenitor markers AP2, PAX3, and PAX7, as well as pan-neural progenitor marker PAX6. While these early progenitor cells were still present at Day 21, also present was a distinct glial population expressing the oligodendrocyte progenitor marker NG2 (Zhang Y, Chen K, Sloan S A, Bennett M L, Scholze A R, O'Keeffe S, Phatnani H P, Guarnieri P, Caneda C, Ruderisch N, Deng S, Liddelow S A, Zhang C, Daneman R, Maniatis T, Barres B A, Wu J Q. An RNA-sequencing transcriptome and splicing database of glia, neurons, and vascular cells of the cerebral cortex. *J Neurosci*. 2014 Sep. 3; 34(36):11929-47).

For human embryonic stem cells differentiated through Day 42 into oligodendrocyte progenitor cells, protein marker expression in the resulting single cell population was characterized by both flow cytometry and ICC.

To characterize protein marker expression of the oligodendrocyte progenitor cells by ICC, staining was carried out as described above for slide-mounted aggregate sections, except permeabilization was performed with 100% methanol for 2 minutes at RT, and blocking solution consisted of 10% fetal bovine serum in PBS.

Figure 5:
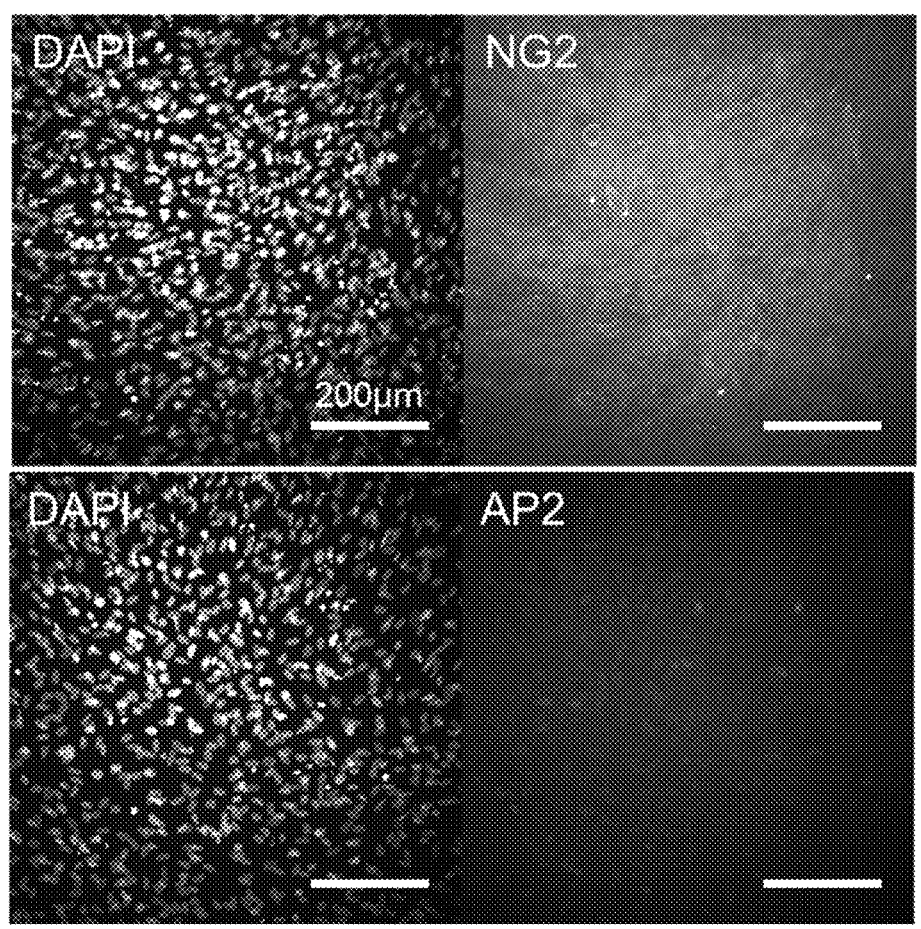
FIG. 5 shows representative photomicrographs of oligodendrocyte progenitor cells generated in accordance with the present disclosure and stained by immunocytochemistry. Oligodendrocyte progenitor cells were stained by immunocytochemistry for DAPI and NG2 (top panels, left to right) and DAPI and AP2 (bottom panels, left to right). Stained cells were imaged on an IN Cell Analyzer 2000. Scale bar represents 200 μm and applies to all images in the figure.

FIG. 5 shows representative ICC data for the Day 42 oligodendrocyte progenitor cells. The resulting single cell population from two representative experiments expressed the oligodendrocyte progenitor cell marker NG2 (Zhang Y, Chen K, Sloan S A, Bennett M L, Scholze A R, O'Keeffe S, Phatnani H P, Guarnieri P, Caneda C, Ruderisch N, Deng S, Liddelow S A, Zhang C, Daneman R, Maniatis T, Barres B A, Wu J Q. An RNA-sequencing transcriptome and splicing database of glia, neurons, and vascular cells of the cerebral cortex. *J Neurosci.* 2014 Sep. 3; 34(36):11929-47) and reduced expression of the dorsal spinal cord progenitor cell marker AP2 (compare FIGS. 3 and 5).

To quantify cell surface markers on Day 42 by flow cytometry, cells were thawed in Thaw Medium (10% fetal bovine serum in DMEM medium), centrifuged and resuspended in Stain Buffer (2% fetal bovine serum/0.05% sodium azide in PBS). Cells were incubated with primary antibodies specific to markers of interest, including NG2 (Invitrogen #37-2300), PDGFRα (BD Biosciences #563575), GD3 (Millipore #MAB2053), A2B5 (BD #563775), CD49f (Millipore #CBL458P), EpCAM (Dako #M080401-2) and CLDN6 (Thermo Fisher #MA5-24076), and their isotype controls for 30 minutes on ice. Cells were washed with Stain Buffer to remove unbound antibodies; in the case of unconjugated antibodies, cells were then incubated with appropriate fluorophore-conjugated secondary antibodies for 30 minutes on ice. Cells were washed and propidium iodide was then added to demark dead cells. In some cases, cells were cultured overnight at 37° C./5% $CO_2$ in tissue culture vessels coated with Matrigel (Corning #356231) to recover protein markers that exhibited sensitivity to the Day 42 harvesting procedure described in Example 4, and were then harvested with TrypLE™ Select (Thermo Fisher #A12859-01) and stained for flow cytometry analysis as described above. All cells were analyzed on an Attune NxT (Thermo Fisher, Waltham, Mass., USA) flow cytometer. To calculate the percentage of cells expressing a given protein marker, dead cells staining with propidium iodine were gated and the number of viable cells bound to the corresponding antibody was expressed as a fraction of the total number of cells analyzed after correcting for the number of cells that exhibited non-specific binding to the isotype control antibody.

TABLE 1 shows representative flow cytometry data for Day 42 oligodendrocyte progenitor cells generated in accordance with the methodology described in Example 5. As shown for two representative runs, a high proportion of cells in the resulting cell population expressed characteristic oligodendrocyte markers, including NG2 and PDGFRα (Zhang Y, Chen K, Sloan S A, Bennett M L, Scholze A R, O'Keeffe S, Phatnani H P, Guarnieri P, Caneda C, Ruderisch N, Deng S, Liddelow S A, Zhang C, Daneman R, Maniatis T, Barres B A, Wu J Q. An RNA-sequencing transcriptome and splicing database of glia, neurons, and vascular cells of the cerebral cortex. *J Neurosci.* 2014 Sep. 3; 34(36):11929-47), and GD3 (Gallo V, Zhou J M, McBain C J, Wright P, Knutson P L, Armstrong R C. Oligodendrocyte progenitor cell proliferation and lineage progression are regulated by glutamate receptor-mediated K+ channel block. *J Neurosci.* 1996 Apr. 15; 16(8):2659-70), as well as the pre-OPC marker, A2B5 (Keirstead H S, Nistor G, Bernal G, Totoiu M, Cloutier F, Sharp K, Steward O. Human embryonic stem cell-derived oligodendrocyte progenitor cell transplants remyelinate and restore locomotion after spinal cord injury. *J Neurosci.* 2005 May 11; 25(19):4694-705). In addition, non-OPC markers were minimally detected in the resulting population, including the neural progenitor/epithelial marker CD49f (Krebsbach P H, Villa-Diaz L G. The Role of Integrin α6 (CD49f) in Stem Cells: More than a Conserved Biomarker. *Stem Cells Dev.* 2017 Aug. 1; 26(15):1090-1099) and the epithelial markers CLDN6 (Lin D, Guo Y, Li Y, Ruan Y, Zhang M, Jin X, Yang M, Lu Y, Song P, Zhao S, Dong B, Xie Y, Dang Q, Quan C. Bioinformatic analysis reveals potential properties of human Claudin-6 regulation and functions. *Oncol Rep.* 2017 August; 38(2):875-885) and EpCAM (Huang L, Yang Y, Yang F, Liu S, Zhu Z, Lei Z, Guo J. Functions of EpCAM in physiological processes and diseases (Review). *Int J Mol Med.* 2018 October; 42(4): 1771-1785).

TABLE 1

Representative flow cytometry data for oligodendrocyte progenitor cells produced by a method in accordance with the present disclosure.

| | OPC/Pre-OPC markers | | | | Non-OPC markers | | |
|---|---|---|---|---|---|---|---|
| | NG2 | PDGFRα | GD3 | A2B5 | CD49f | CLDN6 | EpCAM |
| Run 1 | 92% | 85% | 66% | 39% | 3% | 0% | 0% |
| Run 2 | 98% | 95% | 63% | 89% | 0% | 0% | 2% |

The cell population generated by the methodology described in the present disclosure resulted in higher proportion of cells positive for oligodendrocyte progenitor cell marker NG2 and reduced expression of non-OPC markers CD49f, CLDN6, and EpCAM when compared to OPCs that are currently in clinical testing to treat spinal cord injury and that were generated using another method (Priest C A, Manley N C, Denham J, Wirth E D 3rd, Lebkowski J S. Preclinical safety of human embryonic stem cell-derived oligodendrocyte progenitors supporting clinical trials in spinal cord injury. *Regen Med.* 2015 November; 10(8):939-58; Manley N C, Priest C A, Denham J, Wirth E D 3rd, Lebkowski J S. Human Embryonic Stem Cell-Derived Oligodendrocyte Progenitor Cells: Preclinical Efficacy and Safety in Cervical Spinal Cord Injury. *Stem Cells Transl Med.* 2017 October; 6(10):1917-1929).

Example 6—Characterization of Differentiated Cell Populations by Gene Expression Profiling Gene expression profiling can be used to characterize the cellular phenotype of the starting pluripotent cell population and each stage of differentiation, including the generation of neuroectoderm progenitor cells, glial progenitor cells, and oligodendrocyte progenitor cells. Gene expression profiling includes both global transcriptome profiling, using such methods as microarray and RNA-seq, and targeted gene profiling using methods of increased sensitivity such as quantitative real-time PCR (qPCR).

To perform gene expression profiling, cells were lysed in Qiagen RLT Lysis Buffer (Qiagen #79216), and RNA was purified using Qiagen RNeasy Mini Kit (Qiagen #74106)

according to the manufacturer's guidelines. For qPCR-based analysis, purified RNA was then converted to cDNA according to standard methods using the Invitrogen Superscript IV VILO Mastermix (Thermo Fisher Scientific #11756050) according to the manufacturer's guidelines. The relative expression level of target genes and reference housekeeping genes was then quantified using gene-specific primer-probe sets (Applied Biosystems Taqman Gene Expression Assays, Thermo Fisher Scientific #4331182) according to the manufacturer's guidelines. To determine relative expression levels of a given set of target genes, PCR reactions were performed on the ABI 7900HT Real-Time Sequence Detection System (Applied Biosystems), the BioMark HD System (Fluidigm) or equivalent. Each target gene was normalized to one or multiple reference genes, such as GAPDH, to determine its relative expression level.

TABLE 2 shows qPCR results from two representative experiments measuring expression of pluripotency genes, neuroectoderm progenitor cell genes, glial progenitor cell genes, dorsal spinal cord progenitor cell genes, ventral spinal cord progenitor cell genes, and oligodendrocyte progenitor cell genes in cell populations generated by methods in accordance with the present disclosure. RNA samples were collected at the following time points: prior to differentiation (Day 0), following differentiation to neuroectoderm progenitors (Day 7), following differentiation to glial progenitors (Day 21), and following differentiation to oligodendrocyte progenitors (Day 42). RNA samples were processed for qPCR using the methods described above. A selected panel of genes indicative of each differentiation state were quantified, including: three pluripotency genes (NANOG, LIN28A, SOX2), three neuroectoderm progenitor genes (PAX6, HESS, ZBTB16), three glial progenitor genes (CACGN4, DCC, FABP7), and three oligodendrocyte progenitor genes (CSPG4, PDGFRα, DCN). For each gene, normalized ΔCT values were calculated using the average of five housekeeping genes (ACTB, GAPDH, EP300, PGK1, SMAD1), and fold expression relative to baseline (expression below the limit of quantification) was calculated using the ΔΔCT method.

TABLE 2 qPCR analysis of gene markers for pluripotency, neuroectoderm progenitor cells (NPCs), dorsal spinal cord progenitor cells, ventral spinal cord progenitor cells, glial progenitor cells (GPCs), and oligodendrocyte progenitor cells (OPCs) in H1 uhESCs differentiated into OPCs in accordance with the present disclosure.

| | Run 1 Day 0 uhESC | Run 2 Day 0 uhESC | Run 1 Day 7 NEPC | Run 2 Day 7 NEPC | Run 1 Day 21 GPC | Run 2 Day 21 GPC | Run 1 Day 42 OPC | Run 2 Day 42 OPC |
|---|---|---|---|---|---|---|---|---|
| Pluripotency genes | | | | | | | | |
| NANOG | 158 | 119 | 4 | 3 | 2 | 1 | 2 | 1 |
| LIN28A | 650 | 1684 | 233 | 626 | 5 | 1 | 2 | 1 |
| SOX2 | 480 | 325 | 532 | 243 | 767 | 262 | 2 | 3 |
| Neuroectoderm progenitor cell (NPC) genes | | | | | | | | |
| PAX6 | 1 | 1 | 305 | 250 | 218 | 32 | 2 | 2 |
| HES5 | 1 | 1 | 65 | 71 | 275 | 298 | 6 | 1 |
| ZBTB16 | 1 | 1 | 110 | 120 | 50 | 31 | 2 | 1 |
| Dorsal spinal cord progenitor cell genes | | | | | | | | |
| TFAP2A | 1 | 1 | 67 | 84 | 169 | 215 | 69 | 20 |
| PAX3 | 1 | 1 | 100 | 300 | 91 | 118 | 2 | 7 |
| PAX7 | 1 | 1 | 74 | 178 | 104 | 89 | 19 | 6 |
| Ventral spinal cord progenitor cell genes | | | | | | | | |
| OLIG2 | 1 | 1 | 1 | 1 | 2 | 1 | 2 | 1 |
| NKX2-2 | 1 | 1 | 1 | 1 | 2 | 1 | 2 | 1 |
| Glial progenitor cell (GPC) genes | | | | | | | | |
| CACNG4 | 18 | 11 | 61 | 48 | 268 | 317 | 32 | 15 |
| DCC | 1 | 2 | 17 | 51 | 34 | 324 | 2 | 5 |
| FABP7 | 6 | 10 | 7 | 9 | 17 | 51 | 2 | 4 |
| Oligodendrocyte progenitor cell (OPC) genes | | | | | | | | |
| CSPG4 | 5 | 3 | 5 | 10 | 6 | 49 | 126 | 111 |
| PDGFRα | 1 | 2 | 19 | 20 | 23 | 185 | 584 | 481 |
| DCN | 1 | 1 | 1 | 2 | 285 | 302 | 1080 | 1136 |

Referring to TABLE 2, differentiation of uhESCs for seven days by a method in accordance with the present disclosure resulted in a gene expression profile that was consistent with neuroectoderm progenitor cells, including downregulation of NANOG, and expression of LIN28A, SOX2, PAX6, HESS, and ZBTB16 (Patterson M, Chan D N, Ha I, Case D, Cui Y, Van Handel B, Mikkola H K, Lowry W E. Defining the nature of human pluripotent stem cell progeny. Cell Res. 2012 January; 22(1):178-93; Lippmann E S, Williams C E, Ruhl D A, Estevez-Silva M C, Chapman E R, Coon J J, Ashton R S. Deterministic HOX patterning in human pluripotent stem cell-derived neuroectoderm. Stem Cell Reports. 2015 Apr. 14; 4(4):632-44; Woo S M, Kim J, Han H W, Chae J I, Son M Y, Cho S, Chung H M, Han Y M, Kang Y K. Notch signaling is required for maintaining stem-cell features of neuroprogenitor cells derived from human embryonic stem cells. *BMC Neurosci.* 2009 Aug. 17; 10:97; Avantaggiato V, Pandolfi P P, Ruthardt M, Hawe N, Acampora D, Pelicci P G, Simeone A. Developmental analysis of murine Promyelocyte Leukemia Zinc Finger (PLZF) gene expression: implications for the neuromeric model of the forebrain organization. *J Neurosci.* 1995 July; 15(7 Pt 1):4927-42).

In addition, the neuroectoderm progenitor cells generated after seven days of differentiation exhibited a phenotype that was consistent with dorsal spinal cord progenitor cells based on expression of the dorsal markers TFAP2A (also known as AP2), PAX3, and PAX7 (Le Dréau G, Marti E. Dorsal-ventral patterning of the neural tube: a tale of three signals. Dev Neurobiol. 2012 December; 72(12):1471-81; Marklund U, Alekseenko Z, Andersson E, Falci S, Westgren M, Perlmann T, Graham A, Sundström E, Ericson J. Detailed expression analysis of regulatory genes in the early developing human neural tube. Stem Cells Dev. 2014 Jan. 1; 23(1):5-15). As further evidence of a dorsal spinal cord progenitor cell phenotype, the resulting neuroectoderm progenitor cells did not express the ventral spinal cord progenitor cell markers OLIG2 or NKX2-2, whose expression require activation of the sonic hedgehog signaling pathway (Le Dréau G, Marti E. Dorsal-ventral patterning of the neural tube: a tale of three signals. Dev Neurobiol. 2012 December; 72(12):1471-81; Marklund U, Alekseenko Z, Andersson E, Falci S, Westgren M, Perlmann T, Graham A, Sundström E, Ericson J. Detailed expression analysis of regulatory genes in the early developing human neural tube. Stem Cells Dev. 2014 Jan. 1; 23(1):5-15).

After 21 days of differentiation, the resulting cell population exhibited a gene expression profile that was consistent with glial progenitor cells, including downregulation of pluripotency and neuroectoderm progenitor cell markers and induction of CACNG4, DCC (also known as the netrin receptor), and FABP7 (Zhang Y, Chen K, Sloan S A, Bennett M L, Scholze A R, O'Keeffe S, Phatnani H P, Guarnieri P, Caneda C, Ruderisch N, Deng S, Liddelow S A, Zhang C, Daneman R, Maniatis T, Barres B A, Wu J Q. An RNA-sequencing transcriptome and splicing database of glia, neurons, and vascular cells of the cerebral cortex. *J Neurosci.* 2014 Sep. 3; 34(36):11929-47; Fitzgerald D P, Cole S J, Hammond A, Seaman C, Cooper H M. Characterization of neogenin-expressing neural progenitor populations and migrating neuroblasts in the embryonic mouse forebrain. Neuroscience. 2006 Oct. 27; 142(3):703-16; Rosenzweig S, Carmichael S T. The axon-glia unit in white matter stroke: mechanisms of damage and recovery. *Brain Res.* 2015 Oct. 14; 1623:123-34; Petit A, Sanders A D, Kennedy T E, Tetzlaff W, Glattfelder K J, Dalley R A, Puchalski R B, Jones A R, Roskams A J. Adult spinal cord radial glia display a unique progenitor phenotype. *PLoS One.* 2011; 6(9):e24538. As further evidence of a glial progenitor phenotype, the resulting Day 21 cells exhibited sustained expression of HESS, which in addition to its expression in neuroectoderm progenitor cells/neural progenitor cells (Woo S M, Kim J, Han H W, Chae J I, Son M Y, Cho S, Chung H M, Han Y M, Kang Y K. Notch signaling is required for maintaining stem-cell features of neuroprogenitor cells derived from human embryonic stem cells. *BMC Neurosci.* 2009 Aug. 17; 10:97), HESS has also been shown to promote the neural to glial progenitor switch in the mammalian developing central nervous system (Bansod S, Kageyama R, Ohtsuka T. Hes5 regulates the transition timing of neurogenesis and gliogenesis in mammalian neocortical development. Development. 2017 Sep. 1; 144(17):3156-3167). In addition, the resulting Day 21 glial progenitor cells exhibited sustained expression of the dorsal spinal cord progenitor markers, TFAP2A, PAX3 and PAX7, providing further evidence of derivation from dorsally-patterned neural progenitors.

Following 42 days of differentiation in accordance with the methods described in the present disclosure, the resulting cell population expressed markers consistent with oligodendrocyte progenitors, including downregulation of both the earlier lineage markers and dorsal spinal cord progenitor markers, and induction of CSPG4 (also known as NG2), PDGFRα, and DCN (Zhang Y, Chen K, Sloan SA, Bennett ML, Scholze A R, O'Keeffe S, Phatnani HP, Guarnieri P, Caneda C, Ruderisch N, Deng S, Liddelow S A, Zhang C, Daneman R, Maniatis T, Barres B A, Wu J Q. An RNA-sequencing transcriptome and splicing database of glia, neurons, and vascular cells of the cerebral cortex. *J Neurosci.* 2014 Sep. 3; 34(36):11929-47).

Example 7—Differentiation of Human Embryonic Stem Cells to Dorsal Neuroectoderm Progenitor Cells Using Alternative Small Molecule Inhibitors of MAPK/Erk and BMP Signaling In addition to the small molecule inhibitors used in Example 2 (PD0325901 and Dorsomorphin), alternative small molecule inhibitors of MAPK/ERK and BMP signaling were tested for their ability to differentiate human embryonic stem cells into dorsal neuroectoderm progenitors. TABLE 3 lists the alternative small molecule inhibitors that were tested. Each condition was tested in duplicate wells of a 6-well tissue culture plate.

TABLE 3

Small molecule inhibitors used to differentiate human embryonic stem cells into dorsal neuroectoderm progenitors.

| Inhibitor | Concentration tested | Primary binding target(s) | Vendor catalogue # |
|---|---|---|---|
| MEK-ERK inhibitors | | | |
| PD0325901 | 10 μM | MEK1, MEK2 | ApexBio # A3013 |
| AZD6244 | 10 μM | MEK1, MEK2 | ApexBio # A8207 |
| GSK1120212 | 10 μM | MEK1, MEK2 | ApexBio # A3018 |
| PD184352 | 10 μM | MEK1, MEK2 | ApexBio # A1792 |
| Cobimetinib | 10 μM | MEK1, MEK2 | ApexBio # A3321 |
| BMP inhibitors | | | |
| Dorsomorphin | 2 μM | ALK2, ALK3, ALK6 | Sigma-Aldrich # P5499 |
| ML347 | 2 μM | ALK2, ALK1 | ApexBio # B3688 |

On differentiation Day 7, cells were collected and processed for RNA extraction and gene expression profiling by qPCR as described in Example 6. For each gene, a normalized ΔCT value was calculated relative to the average of five housekeeping genes (ACTB, GAPDH, EP300, PGK1, SMAD1), and fold expression relative to baseline (expression below the limit of quantification) was calculated using the ΔΔCT method. TABLE 4 shows the average of fold expression value for biological duplicates of each small molecule combination (relative to baseline). Referring to TABLE 4, differentiation of uhESCs for seven days with each of the tested small molecule combinations resulted in downregulation of the pluripotency marker NANOG and a similar degree of maintained expression or induction of genes associated with a neuroectoderm progenitor cell phenotype, including LIN28A, SOX2, PAX6, HESS, and ZBTB16. In addition, each of the tested small molecule combinations resulted in a dorsal spinal cord progenitor phenotype based on expression of the dorsal markers, TFAP2A, PAX3, and PAX7, and a lack of expression of the ventral markers, OLIG2 and NKX2-2.

Figure 6:
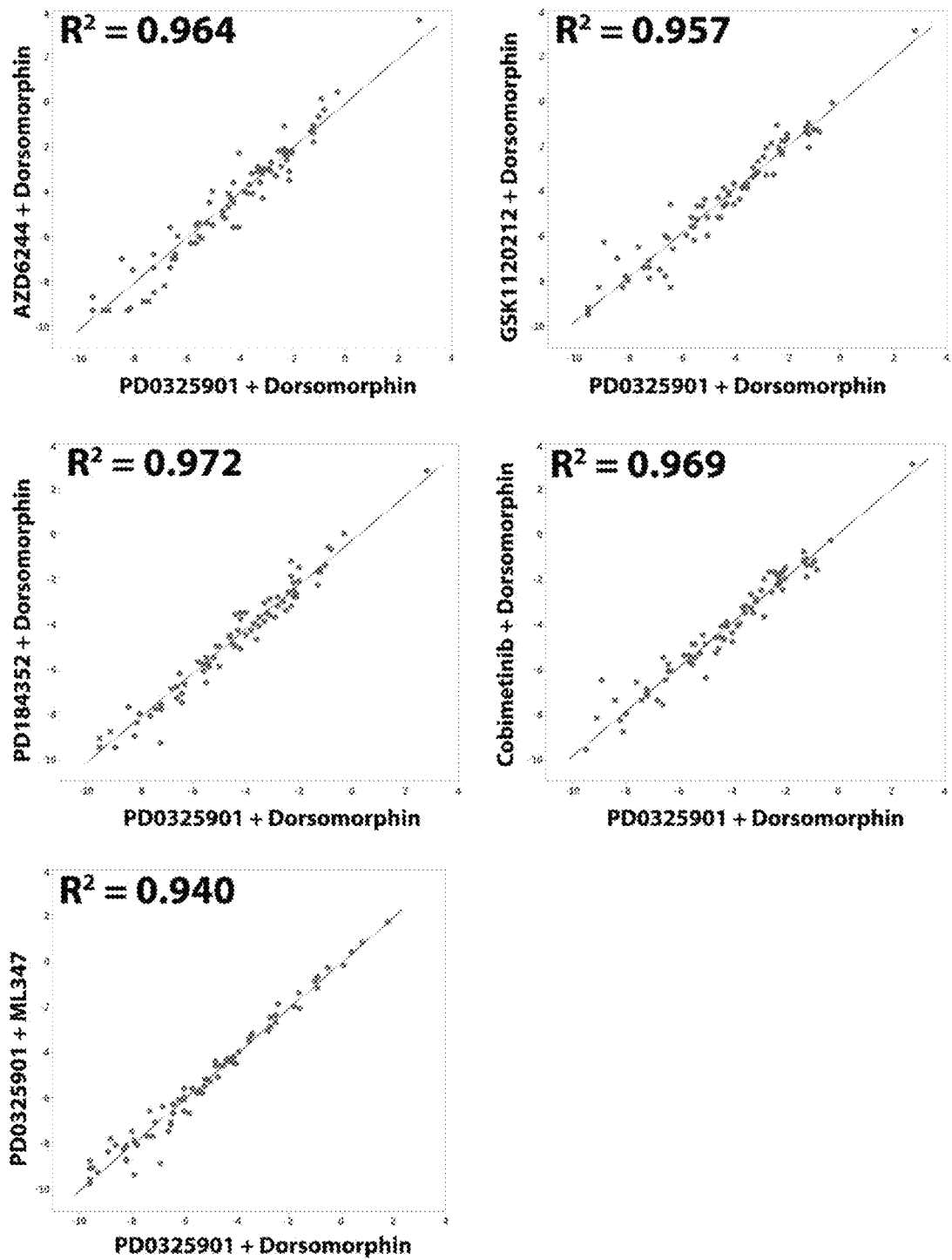
FIG. 6 shows correlation plots of the Day 7 gene expression profile of uhESCs differentiated into dorsal neuroectoderm progenitor cells (dNPCs) using different small molecule combinations. Each correlation plot shows a comparison of the Day 7 gene expression profile for cells treated with PD0325901 plus Dorsomorphin versus the alternative small molecule combination indicated on the y-axis of each plot. For each plot, the data points represent each of the 96 genes assessed by Fluidigm qPCR and calculated as the normalized ΔCT as described in Example 7. R-squared values are shown in the upper left corner of each plot and were calculated based on the best-fit line using JMP software (SAS, Cary, N.C., USA).

To obtain a more comprehensive comparison of the resulting Day 7 cellular phenotypes after treatment with each small molecule combination, Fluidigm qPCR was conducted using a 96 gene panel that consisted of known markers for pluripotency, neuroectoderm progenitor cells, neural tube patterning, glial progenitor cells, oligodendrocyte progenitor cells, neural crest cells, neurons, astrocytes, pericytes, Schwann cells, and epithelial cells. Referring to FIG. 6, comparison of the day 7 cellular phenotype for each alternative small molecule combination to the cellular phenotype generated by treatment with PD0325901 plus Dorsomorphin by regression plot of the normalized ΔCT values indicated that a similar overall cellular phenotype could be achieved with each of the small molecule combinations tested. Taken together, the results shown in TABLE 4 and FIG. 6 support that various combinations of: (i) a MAPK/ERK inhibitor, together with (ii) a BMP signaling inhibitor, (iii) in the absence of a SHH signaling activator, can be used to differentiate uhESCs to dorsal neuroectoderm progenitor cells, and further to glial progenitor cells and to oligodendrocyte progenitor cells using the methods of the present disclosure.

in 4% paraformaldehyde (PFA) for 5 minutes on ice and permeabilized in blocking buffer overnight. Subsequently, cysts were stained for CD49f (ITGA6), phalloidin, and counter-stained with DAPI. Cysts were imaged using IN Cell Analyzer 2000 (GE Healthcare Life Sciences) and cyst frequency, size and staining intensity were quantified using IN Cell Developer Software (GE Healthcare Life Sciences) and MATLAB™ (Mathworks). Referring to TABLE 5, OPCs generated from two representative runs using a method in accordance with the present disclosure and tested in the in vitro cyst assay produced no detectable cysts per 100,000 cells. In contrast, three control lots of OPCs (Control A, Control B and Control C) that were generated by an alternative method previously found to give rise to epithelial cyst formation in vivo (Manley N C, Priest C A, Denham J, Wirth E D 3rd, Lebkowski JS. Human Embryonic Stem Cell-Derived Oligodendrocyte Progenitor Cells: Preclinical

TABLE 4 qPCR analysis of gene markers for pluripotency and neuroectoderm progenitor cells (NPCs) in H1 uhESCs differentiated into NPCs using different combinations of small molecule inhibitors.

| | PD0325901 + Dorso | AZD6244 + Dorso | GSK1120212 + Dorso | PD184352 + Dorso | Cobimetinib + Dorso | PD0325901 + ML347 |
|---|---|---|---|---|---|---|
| Pluripotency genes | | | | | | |
| NANOG | 1 | 4 | 1 | 1 | 1 | 1 |
| LIN28A | 548 | 618 | 606 | 635 | 504 | 488 |
| SOX2 | 370 | 484 | 254 | 401 | 201 | 202 |
| Neuroectoderm progenitor cell genes | | | | | | |
| PAX6 | 363 | 539 | 258 | 417 | 173 | 156 |
| HES5 | 97 | 100 | 68 | 91 | 36 | 36 |
| ZBTB16 | 135 | 149 | 145 | 171 | 134 | 120 |
| Dorsal spinal cord progenitor cell genes | | | | | | |
| TFAP2A | 67 | 61 | 84 | 43 | 100 | 166 |
| PAX3 | 112 | 99 | 180 | 84 | 193 | 158 |
| PAX7 | 156 | 106 | 186 | 100 | 148 | 209 |
| Ventral spinal cord progenitor cell genes | | | | | | |
| OLIG2 | 1 | 1 | 1 | 1 | 1 | 1 |
| NKX2-2 | 1 | 1 | 1 | 1 | 1 | 1 |

Example 8—Assessing the Presence of Extraneous Epithelial Lineage Cells in the Differentiated OPC Population Using an In Vitro Cyst Assay Presence of undesirable epithelial lineage cells in an OPC population generated in accordance with the present disclosure was tested using an in vitro cyst assay. The cyst assay was performed essentially according to a protocol by Debnath et al. (Debnath J, Muthuswamy S K, Brugge J S. Morphogenesis and oncogenesis of MCF-10A mammary epithelial acini grown in three-dimensional basement membrane cultures. 2003 Methods. 3:256-68). Briefly, OPCs were grown in a 3D culture system in the presence of factors known to stimulate epithelial cyst formation for a period of 20 days. In addition to visual detection of cysts, the presence of cystic structures containing basolateral protein expression of the epithelial marker CD49f was also assessed using immunocytochemistry.

OPCs were seeded in cyst-supporting media onto a pad of Matrigel® (Corning) at a density of $21.9 \times 10^3$ cells/cm2 (in total, $0.5 \times 10^6$ cells were seeded in 12 wells of a 24 well plate). Cells were cultured for 20 days. On Day 20, a live cyst count was performed, Matrigel® was dissolved using Cell Recovery Solution (Corning #354253), cells were fixed Efficacy and Safety in Cervical Spinal Cord Injury. *Stem Cells Transl Med.* 2017 October; 6(10):1917-1929) did give rise to cysts in the assay.

TABLE 5

Representative cyst assay results for oligodendrocyte progenitor cells produced by a method in accordance with the present disclosure.

| | Control A | Control B | Control C | Run 1 | Run 2 |
|---|---|---|---|---|---|
| Cysts/100,000 cell input | 6.2 | 16.8 | 25.6 | 0 | 0 |

Figure 2A:
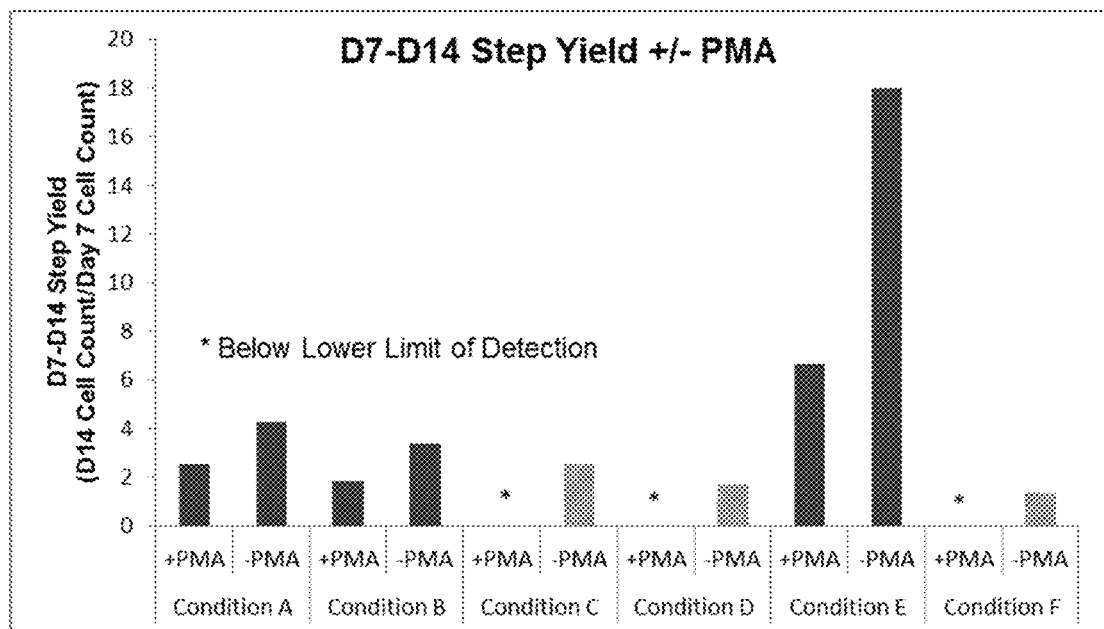
FIGS. 2A-2C show representative data depicting the effect of absence of SHH or a SHH signaling agonist on the cell yield.

Example 9—Comparison of Differentiated Cell Yield in the Presence Vs. Absence of SHH Signaling Activator In testing various small molecule differentiation regimens, it was discovered that removal of SHH signaling activators, such as Purmorphamine (PMA) from the differentiation process consistently lead to an increase of step yield of cells between Days 7 and 14 (FIG. 2A). Because PMA and other SHH signaling agonists drive the ventrilization of early spinal cord progenitors (Kutejova E, Sasai N, Shah A, Gouti M, Briscoe J. Neural Progenitors Adopt Specific Identities by Directly Repressing All Alternative Progenitor Transcriptional Programs. Dev Cell. 2016 Mar. 21; 36(6):639-53), this suggests that the culture conditions present from Day 7 to Day 14 are favorable to the expansion of neural progenitors of a more dorsal phenotype. Surprisingly, it was found this early dorsal phenotype, despite not being the region of early OPC generation in vivo, still results in OPC cells at Day 42 (FIG. 5).

Figure 2B:
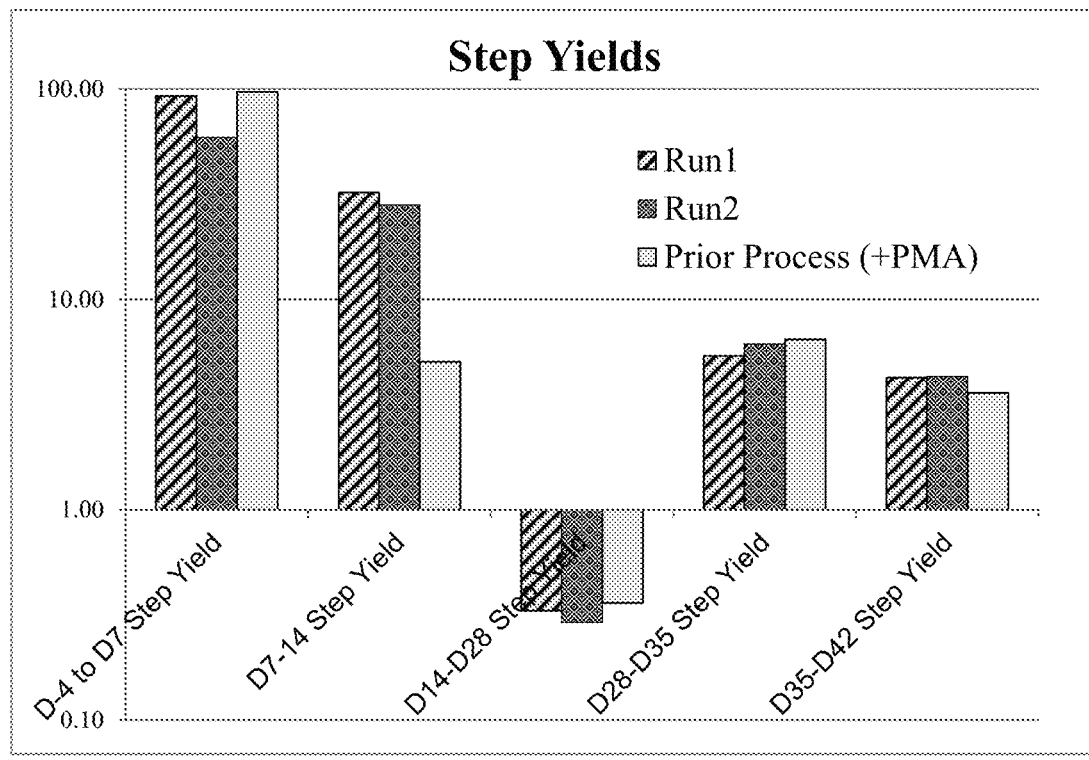
Figure 2C:
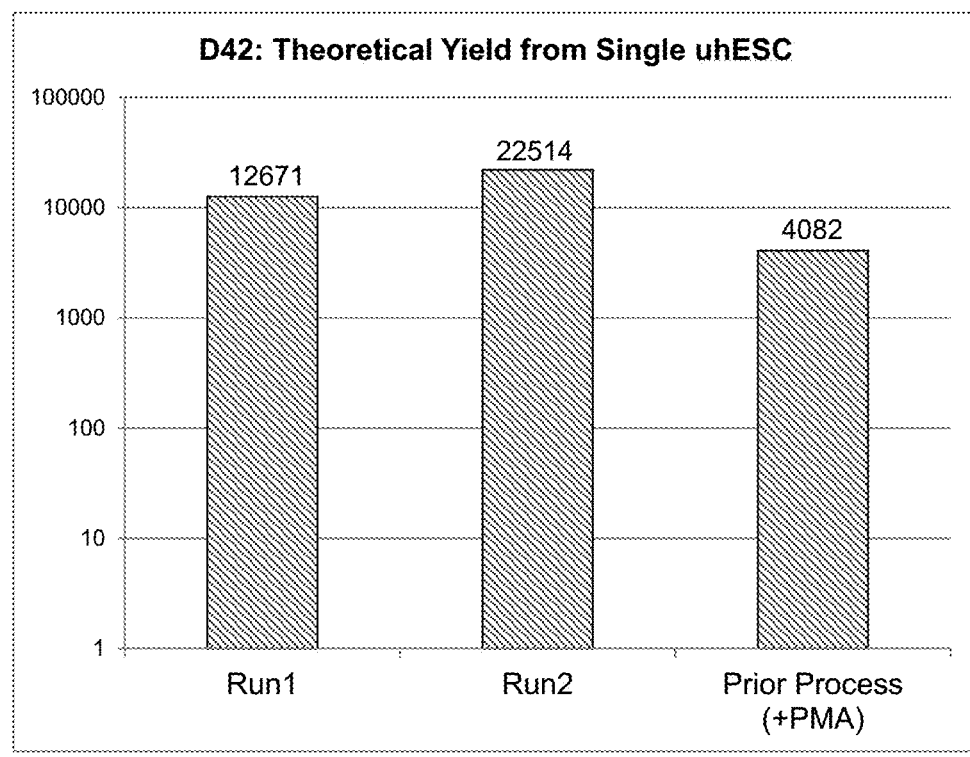

The impact of removal of SHH signaling activators from the differentiation process in accordance with the present disclosure was further tested and quantified. In two representative experiments in which SHH agonist PMA was removed from the differentiation process, (Run1 and Run2), step yields from Day 7 to Day 14 increased when compared to a run that contained PMA (FIG. 2B). This led to a substantial increase in overall theoretical cell yield (FIG. 2C).

Example 10—In Vitro Functional Bioassays (Decorin Secretion and Migration Assay)

Decorin is a naturally occurring extracellular small leucine-rich proteoglycan TGF-β1/2 antagonist, which regulates diverse cellular functions through interactions with components of the extracellular matrix (ECM). Decorin expressed by neurons and astrocytes in the central nervous system attenuates scar tissue, blocks cavitation and promotes wound healing via its anti-scarring effects that significantly lower the build-up of titres of scar-derived axon growth inhibitors by degradation and suppression of their synthesis [Ahmed, Z., et al., *Decorin blocks scarring and cystic cavitation in acute and induces scar dissolution in chronic spinal cord wounds*. Neurobiol Dis, 2014. 64: p. 163-76]. Human recombinant protein was shown by itself when added exogenously to have a beneficial effect in animal models of spinal cord injury [Wu, L., et al., *Combined transplantation of GDAs(BMP) and hr-decorin in spinal cord contusion repair*. Neural Regen Res, 2013. 8(24): p. 2236-48].

Long term stability data of three manufactured GPOR-OPC1 clinical batches demonstrates a secretion levels of ~15-30 ng/ml.

In this in-vitro assay, decorin production by OPC1 cells is measured using commercial manufactured solid phase sandwich ELISA kit. The test material for the potency assay is a supernatant that is generated by thawing a vial(s) of OPC1 drug product cells, culturing the cells for 48 hours, harvesting the conditioned medium (CM) and storing those CM supernatants frozen until time of testing by ELISA. On-going OPC1 process development studies show that the levels of decorin secretion post 48 hours of in vitro culturing of improved process OPC1 cells is similar to those of GPOR-OPC1 batches (as described above) and is within the range of ~20-35 ng/ml.

One of the hallmarks of OPC1 activity in vivo as exemplified in the rat cervical SCI model is the in vivo migration of OPC1 cells from the site(s) of injection into the injured and surrounding areas of the cavitation in the spinal cord. The migration assay is based on in vitro measurement of migration of OPC1 cells in response to the different chemotactic factor, such as PDGFαα and PDGFββ [Armstrong, R. C., L. Harvath, and M. E. Dubois-Dalcq, *Type 1 astrocytes and oligodendrocyte-type 2 astrocyte glial progenitors migrate toward distinct molecules*. J Neurosci Res, 1990. 27(3): p. 400-7; Milner, R., et al., *Contrasting effects of mitogenic growth factors on oligodendrocyte precursor cell migration*. Glia, 1997. 19(1): p. 85-90; Sanchez-Rodriguez, M. A., et al., *The endocannabinoid 2-arachidonoylglycerol regulates oligodendrocyte progenitor cell migration*. Biochem Pharmacol, 2018. 157: p. 180-188].

In this in-vitro assay, OPC-1 cells are seeded on individual wells of a transwell systems (Corning™ Transwell™ Polycarbonate Membrane Inserts, 8 μm pore size). Cells are exposed to medium in the lower well which either contains chemoattractant factor (PDGFββ), or not. After an overnight incubation, the cells that migrate through the transwell are harvested and counted to determine the % of input cells that migrated which is then reported as the % of Migration. This method is currently under a research phase and further studies are performed in order to evaluate and improve method's performance. On-going OPC1 process development studies show that the % of in vitro migration of OPC1 cells in response to stimulus with PDGFββ chemoattractant for 16-24 hours is within the range of ~15-50%.

Assessment of OPC1 in vitro function using decorin secretion and migration bioassays shows that higher decorin secretion and higher percentage of migration were observed for improved process OPC1 batches that demonstrated higher purity (flow cytometry analysis of biomarker expression), better yield and superior morphology assessment and vice versa; lower decorin secretion and lower percentage of migration were observed for OPC1 batches that demonstrated lower purity, lower yield and inferior morphology assessment.

For example, TABLE 6 provides a summary of a Day 42 final product characterized by marker data, decorin secretion and migration bioassays.

TABLE 6

| | Day 42 - final product | | | | | | | |
|---|---|---|---|---|---|---|---|---|
| Protocol # | CD24 PE | Claudin 6 | EpCAM DL488 | GD3 | NG2 | PDGFRα | % Migration (+PDGFββ) | Decorin (ng/ml) |
| Run #1 | 15.8 | 1 | 1.35 | 69 | 91 | 96.9 | 40% | 32.20 |
| Run #2 | 8.77 | 0.8 | 0.55 | 47.7 | 81.4 | 93.7 | 46% | 31.80 |

While the present disclosure has been described with reference to particular embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all aspects falling within the scope and spirit of the appended claims.

What is claimed is:

1. A method for obtaining a population of cells comprising dorsal neural progenitor cells (dNPCs) from undifferentiated human pluripotent stem cells, the method comprising:
   a) obtaining a culture of undifferentiated human pluripotent stem cells;
   b) culturing the undifferentiated human pluripotent stem cells adherently in the presence of at least one inhibitor of mitogen-activated protein kinase/extracellular signal-regulated kinase (MAPK/ERK), at least one inhibitor of bone morphogenetic protein (BMP) signaling and retinoic acid for a first time period, thereby inducing differentiation to neuroectoderm; and
   c) culturing the cells from b) adherently in the presence of retinoic acid and in the absence of sonic hedgehog (SHH) or a SHH signaling activator for a second time period, thereby obtaining dorsal neural progenitor cells.

2. The method of claim 1, further comprising an additional step of harvesting the cells from c), replating the harvested cells on a substrate and further culturing the cells adherently in the presence of basic fibroblast growth factor (bFGF) and epidermal growth factor (EGF) for a further time period, thereby expanding the neural progenitor cells.

3. The method of claim 2, further comprising an additional step of harvesting the expanded cells and culturing them further as aggregates in suspension in the presence of bFGF and EGF for a further time period, until the cells have matured into glial progenitor cells.

4. The method of claim 3, further comprising an additional step of plating down the aggregates comprising glial progenitor cells on a substrate and culturing the cells adherently for a further time period in the presence of epidermal growth factor (EGF), optionally splitting the cells from time to time, until the cells have matured into oligodendrocyte progenitor cells (OPCs).

5. The method of claim 3, further comprising an additional step of plating down the aggregates comprising glial progenitor cells on a substrate and culturing the cells adherently for a further time period in the presence of platelet-derived growth factor AA (PDGF-AA) and EGF, optionally splitting the cells from time to time, until the cells have matured into oligodendrocyte progenitor cells (OPCs).

6. The method of claim 3, wherein the cells are cryopreserved at a stage in the method and subsequently thawing the cells and proceeding with the method.

7. The method of claim 1, in which the substrate is recombinant human laminin-521.

8. The method of claim 1, wherein the human pluripotent stem cells are human embryonic stem cells (hESCs).

9. The method of claim 1, wherein the human pluripotent stem cells are human induced pluripotent stem cells (hiPSCs).

10. The method of claim 1, wherein the at least one inhibitor of MAPK/ERK kinase is selected from the group consisting of PD0325901, AZD6244, GSK1120212, PD184352 and Cobimetinib.

11. The method of claim 1, wherein the at least one inhibitor of MAPK/ERK kinase is PD0325901.

12. The method of claim 1, wherein the at least one inhibitor of BMP signaling is an inhibitor of activin receptor-like kinase 2 (ALK2).

13. The method of claim 1, wherein the at least one inhibitor of BMP signaling is selected from the group consisting of Dorsomorphin, DMH-1, K02288, ML347, LDN193189 and Noggin protein.

14. The method of claim 1, wherein the at least one inhibitor of BMP signaling is Dorsomorphin.

15. The method of claim 1, wherein the first period is about three to four days.

16. The method of claim 1, wherein the second period is about three to four days.

17. The method of claim 3, wherein the aggregates are cultured in suspension for about seven days.

18. The method of claim 4, wherein the cells are cultured adherently after the plate-down of aggregates for about twenty-one days.

19. A method for obtaining a population of cells comprising oligodendrocyte progenitor cells (OPCs) from undifferentiated human pluripotent stem cells, the method comprising:
   a) obtaining dorsal neural progenitor cells (dNPCs) according to the method of claim 1;
   b) harvesting the cells from a), replating them on a substrate and culturing the cells adherently in the presence of basic fibroblast growth factor (bFGF) and epidermal growth factor (EGF) for a further time period, thereby expanding the neural progenitor cells;
   c) harvesting the cells from b) and further culturing the cells as aggregates in suspension in the presence of bFGF and EGF for a further time period, until the cells have matured into dorsal glial progenitor cells; and
   d) plating down the aggregates from c) on a substrate and culturing the cells adherently for a further time period in the presence of epidermal growth factor (EGF), optionally splitting the cells from time to time, until the cells have matured into OPCs;
   wherein the OPCs express one or more markers selected from neural/glial antigen 2 (NG2), platelet-derived growth factor receptor A (PDGFRa), and ganglioside GD3 (GD3).

20. The method of claim 19, wherein the adherent culturing is performed on a substrate selected from: (i) a cell adhesion peptide and (ii) an extracellular matrix selected from laminin and vitronectin.

21. The method of claim 19, wherein the adherent culturing is performed on recombinant human laminin-521.

22. The method of claim 19, wherein the adherent culturing is performed on laminin-511 E8 fragment.

23. The method of claim 19, wherein step c) is performed in dynamic suspension.

24. The method of claim 19, wherein during step d), the media additionally comprises platelet-derived growth factor AA (PDGF-AA).

25. The method of claim 19, wherein the human pluripotent stem cells are hESCs.

26. The method of claim 19, wherein the human pluripotent stem cells are hiPSCs.

27. The method of claim 19, wherein the OPCs are cryopreserved and ready for administration to a subject upon thawing.

* * * * *